(12) United States Patent
Mototsu

(10) Patent No.: US 8,926,901 B2
(45) Date of Patent: Jan. 6, 2015

(54) SAMPLE ANALYZER

(75) Inventor: Kazunori Mototsu, Kobe (JP)

(73) Assignee: Sysmex Corporation, Hyogo (JP)

( * ) Notice: Subject to any disclaimer, the term of this patent is extended or adjusted under 35 U.S.C. 154(b) by 109 days.

(21) Appl. No.: 13/051,410

(22) Filed: Mar. 18, 2011

(65) Prior Publication Data

US 2011/0236259 A1 Sep. 29, 2011

(30) Foreign Application Priority Data

Mar. 29, 2010 (JP) ................. 2010-074202

(51) Int. Cl.
*G01N 35/02* (2006.01)
*G01N 35/04* (2006.01)
*B01L 3/00* (2006.01)
*B01L 9/00* (2006.01)
*G01N 35/00* (2006.01)

(52) U.S. Cl.
CPC ........... *B01L 3/52* (2013.01); *G01N 2035/0443* (2013.01); *G01N 2035/00772* (2013.01); *B01L 3/545* (2013.01); *B01L 9/00* (2013.01); *B01L 2300/022* (2013.01); *B01L 2300/027* (2013.01); *B01L 2300/0809* (2013.01); *B01L 2300/0841* (2013.01); *B01L 2300/1822* (2013.01); *B01L 2300/1844* (2013.01); *G01N 35/00732* (2013.01); *G01N 35/0098* (2013.01); *G01N 2035/00782* (2013.01); *G01N 2035/00811* (2013.01); *G01N 2035/0415* (2013.01); *G01N 2035/0444* (2013.01); *G01N 35/025* (2013.01)
USPC .................... 422/64; 422/63; 436/43; 436/45

(58) Field of Classification Search
CPC .............. G01N 35/00732; G01N 2035/00772; G01N 2035/00782
See application file for complete search history.

(56) References Cited

U.S. PATENT DOCUMENTS

| | | | |
|---|---|---|---|
| 2002/0190126 A1* | 12/2002 | Benhammou et al. | 235/451 |
| 2004/0258565 A1* | 12/2004 | Watari | 422/64 |
| 2008/0085215 A1* | 4/2008 | Mototsu et al. | 422/68.1 |
| 2010/0073141 A1* | 3/2010 | Nishida et al. | 340/10.3 |
| 2010/0127939 A1 | 5/2010 | Yusa | |
| 2011/0223062 A1* | 9/2011 | Minemura et al. | 422/67 |

FOREIGN PATENT DOCUMENTS

| | | |
|---|---|---|
| JP | 2004-093518 | 3/2004 |
| JP | 2005-009863 | 1/2005 |
| JP | 2005-125144 | 5/2005 |
| JP | 2007-081825 | 3/2007 |
| JP | 4035706 B2 | 1/2008 |

(Continued)

*Primary Examiner* — P. Kathryn Wright
(74) *Attorney, Agent, or Firm* — Sughrue Mion, PLLC

(57) ABSTRACT

A sample analyzer that analyzes a sample by using a reagent contained in a reagent container is disclosed. The sample analyzer includes a container holding unit which is configured to hold a plurality of reagent containers, and a plurality of electronic tags is attached to the plurality of reagent containers, on which a reagent information regarding reagents is recorded. The sample analyzer further includes an antenna section which emits a radio wave to an electronic tag of a reagent container. A range of the radio wave emitted from the antenna section to the electronic tag is limited to a predetermined range or by a limiting member which is arranged between the antenna section and the electronic tag of the reagent container, and which is configured to limit a range of the radio wave emitted from the antenna section to the electronic tag.

11 Claims, 23 Drawing Sheets

(56) References Cited

FOREIGN PATENT DOCUMENTS

| JP | 2008-140216 A | 6/2008 |
| JP | 2008-203007 * | 9/2008 |
| JP | 2009-210444 A | 9/2009 |
| WO | 2008/136408 A1 | 11/2008 |
| WO | WO 2010/058736 * | 5/2010 |

* cited by examiner

SAMPLE ANALYZER

FIELD OF THE INVENTION

The present invention relates to a sample analyzer, and in particular, to a sample analyzer mounting a reagent container with an electronic tag on which reagent information is recorded.

BACKGROUND

A sample analyzer mounting a reagent container with an electronic tag on which reagent information is recorded is conventionally known.

Japanese Patent Publication No. 2009/210444 discloses an automatic analyzer including a reagent container holding unit for holding a plurality of reagent containers with wireless IC tags on which reagent information is recorded, an antenna section for receiving radio wave from the wireless IC tag, an information reading/recording unit for receiving the radio wave returned from the wireless IC tag from the antenna section, and a sensor for detecting the presence of the reagent container at a position facing the antenna section. This automatic analyzer is configured to perform a reading operation of the reagent information when the reagent container is positioned at the position facing the antenna section. The automatic analyzer does not emit a signal from the information reading/recording unit to the antenna section and does not perform a reading operation of reagent information when the reagent container is not positioned at the position facing the antenna section.

In an analyzer in which a plurality of reagent containers is lined and held, reagent information may be read from a plurality of electronic tags with one reading operation, in which case it becomes difficult to determine which reagent information has been read from which target electronic tag.

For instance, in the automatic analyzer described in Japanese Patent Publication No. 2009/210444, it becomes difficult to determine which reagent information has been read from the electronic tag of the reagent container positioned at the position facing the antenna section if a reagent information has been read from a wireless IC tag of another reagent container adjacent to the reagent container positioned at the position facing the antenna section. To avoid this, a large arrangement interval between the reagent containers needs to be ensured, whereby the device main body enlarges by such amount.

SUMMARY

The scope of the present invention is defined solely by the appended claims, and is not affected to any degree by the statements within this summary.

A first aspect of the present invention is a sample analyzer for analyzing a sample using a reagent in a reagent container, comprising: a reagent container holding unit configured to hold a plurality of reagent containers, wherein an electronic tag, on which a reagent information regarding a reagent is recorded, is attached to each of the plurality of reagent containers; an antenna section configured to emit a radio wave to an electronic tag of a reagent container held by the reagent container holding unit; and a limiting member which is arranged between the antenna section and the electronic tag of the reagent container held by the reagent container holding unit, and which is configured to limit a range of the radio wave emitted from the antenna section to the electronic tag.

A second aspect of the present invention is a sample analyzer for analyzing a sample using a reagent in a reagent container, comprising; a reagent container holding unit configured to hold a plurality of reagent containers, wherein an electronic tag, on which a reagent information regarding a reagent is recorded, is attached to each of the plurality of reagent containers; and an antenna section configured to emit a radio wave to an electronic tag of a reagent container held by the reagent container holding unit, wherein a range of the radio wave emitted from the antenna section to the electronic tag is limited to a predetermined range.

DETAILED DESCRIPTION OF THE EMBODIMENT

The embodiments embodying the present invention will be described below based on the drawings.
(First Embodiment)

First, the configuration of a sample analyzer 1 according to a first embodiment of the present invention will be described with reference to FIG. 1 to FIG. 22.

The sample analyzer 1 according to the first embodiment of the present invention is an apparatus for carrying out examinations on various items such as a protein related to an infectious disease (e.g., hepatitis B, hepatitis C, etc.), a tumor marker, and a thyroid hormone, using samples such as blood.

The sample analyzer 1 is an apparatus for performing quantitative measurement or qualitative measurement on the antigen, the antibody, and the like contained in a sample (blood specimen) such as blood, which is the measurement target. When quantitatively measuring the antigen contained in the sample, the sample analyzer 1 is configured such that magnetic particles (R2 reagent) are bonded to a capture antibody (R1 reagent) which is bonded to an antigen contained in a sample, and thereafter, the bound antigen, capture antibody, and magnetic particles are attracted to a magnet (not shown) of a primary BF (Bound Free) separator 11 to remove the R1 reagent containing non-reactive (free) capture antibody. The sample analyzer 1 bonds the antigen bound with the magnetic particles and a labeled antibody (R3 reagent), and thereafter, attracts the bound magnetic particles, the antigen, and the labeled antibody to a magnet of a secondary BF separator 12 to remove a R3 reagent containing non-reactive (free) labeled antibody. Furthermore, a dispersion liquid (R4 reagent) and a light emitting substrate (R5 reagent) that emits light in the reaction process with the labeled antibody are added, and a light emitting amount generated through the reaction of the labeled antibody and the light emitting substrate is measured. The antigen contained in the sample that bonds with the labeled antibody is quantitatively measured through such processes.

Figure 1:
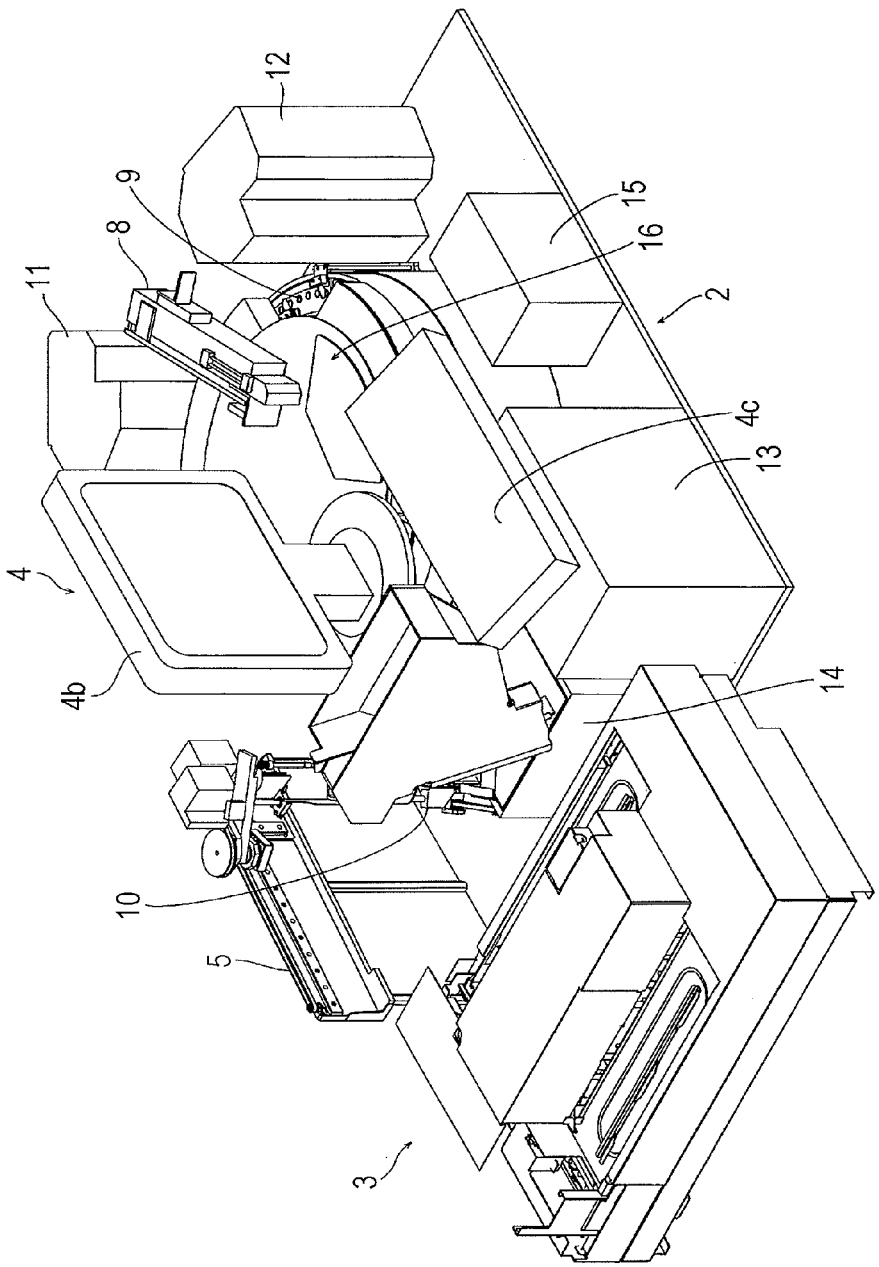
FIG. 1 is a perspective view showing an overall configuration of a sample analyzer according to a first embodiment of the present invention.
Figure 2:
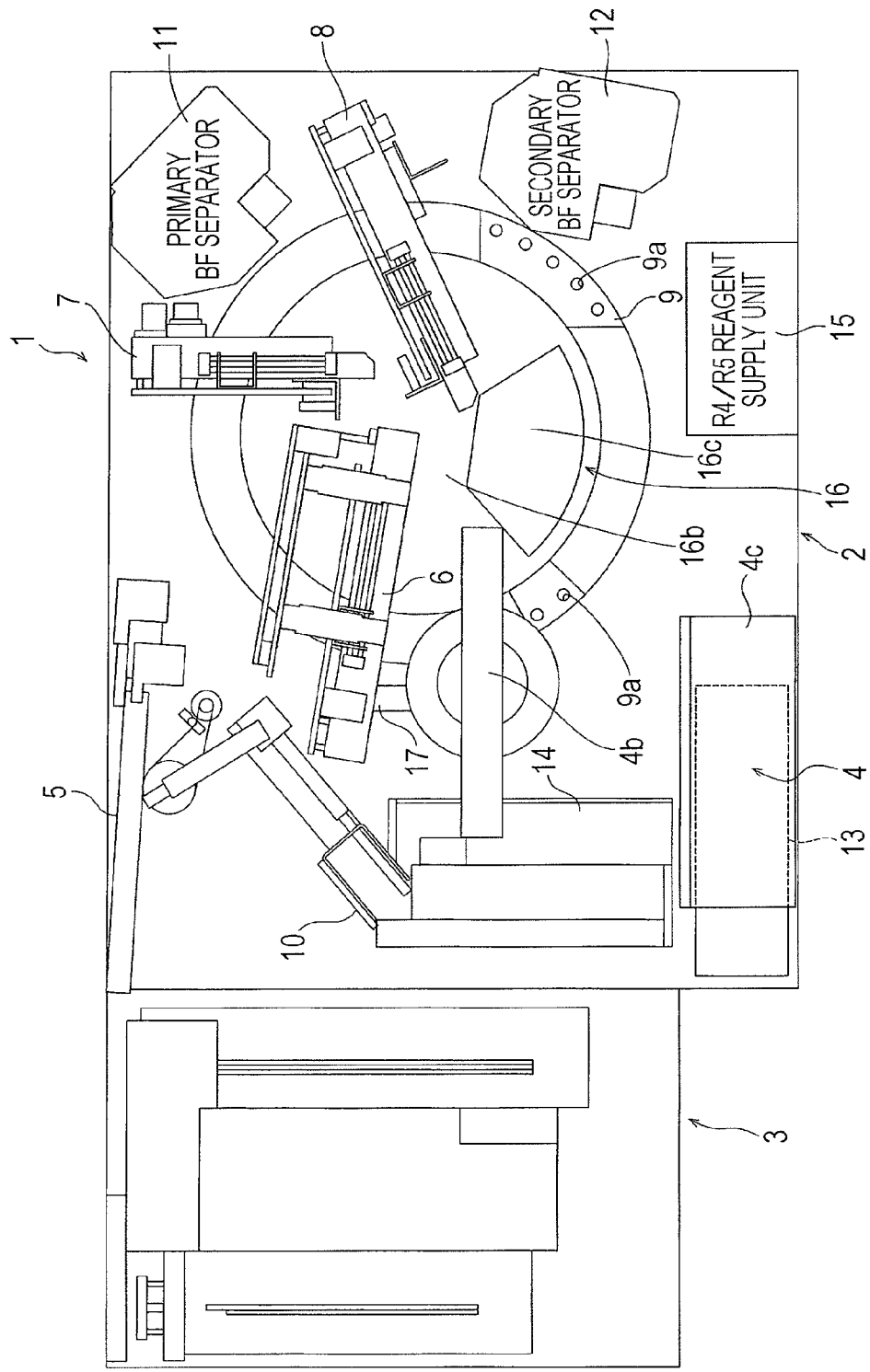
FIG. 2 is a plan view showing the overall configuration of the sample analyzer according to the first embodiment shown in FIG. 1.

As shown in FIGS. 1 and 2, the sample analyzer 1 includes a measurement mechanism section 2, a sample transport section (sampler) 3 arranged adjacent to the measurement mechanism section 2, and a control device 4 including PC (personal computer) electrically connected to the measurement mechanism section 2.

The sample transport section 3 is configured to transport a rack mounted with a plurality of test tubes (not shown) containing samples. The sample transport section 3 is configured to transport the test tube containing the sample to a sample aspirating position by a sample dispensing arm 5.

Figure 3:
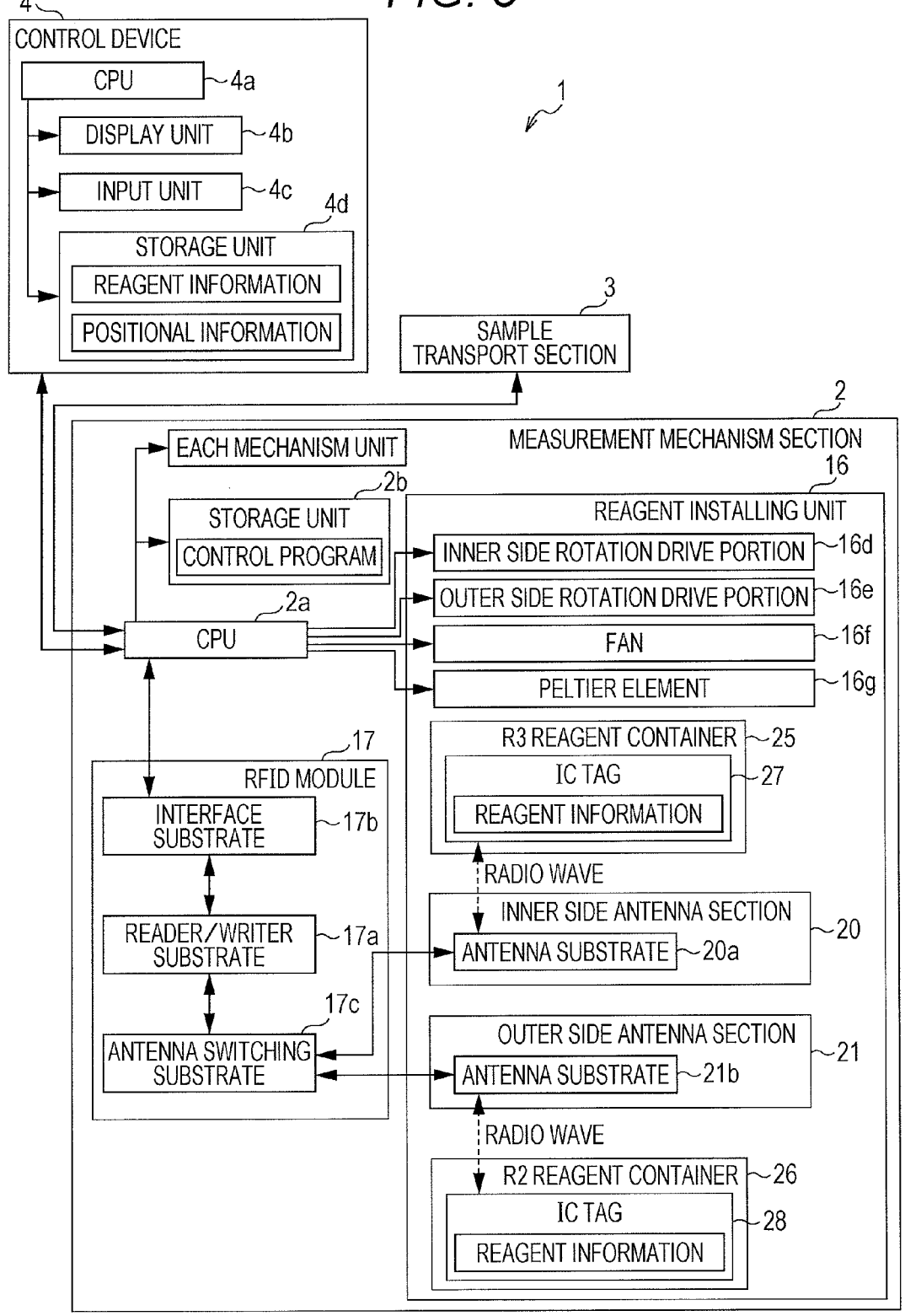
FIG. 3 is a block diagram for describing the configuration of the sample analyzer according to the first embodiment shown in FIG. 1.
Figure 4:
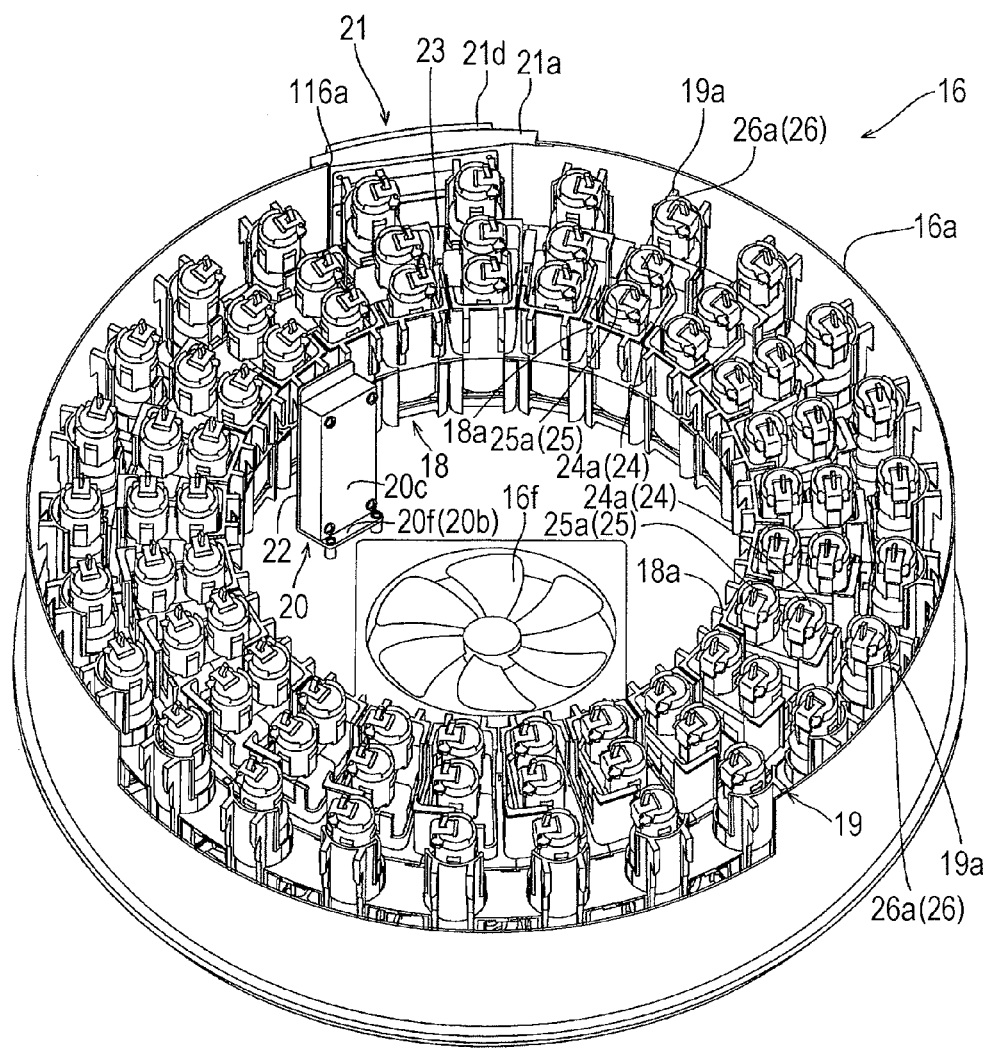
FIG. 4 is a perspective view showing the interior of a reagent installing unit of the sample analyzer according to the first embodiment shown in FIG. 1.

As shown in FIG. 3, the control device 4 includes a CPU 4a, a display unit 4b, an input unit 4c, and a storage unit 4d. The CPU 4a causes the measurement mechanism section 2 (CPU 2a described below) to perform a measurement based on measurement conditions and the like input by the user using the input unit 4c, and analyzing the measurement result obtained by the measurement mechanism section 2 and displaying the analysis result on the display unit 4b. The storage unit 4d includes a hard disc, and individually stores the reagent information and the positional information of each of an R1 reagent container 24, an R3 reagent container 25, and an R2 reagent container 26 described below. The storage unit 4d is described in detail below.

As shown in FIG. 2, the measurement mechanism section 2 is configured by the sample dispensing arm 5, an R1 reagent dispensing arm 6, an R2 reagent dispensing arm 7, an R3 reagent dispensing arm 8, a reaction unit 9, a cuvette supplying unit 10, a primary BF separator 11, a secondary BF separator 12, a pipette tip supplying unit 13, a detector 14, an R4/R5 reagent supplying unit 15, a reagent installing unit 16, and an RFID (Radio Frequency Identification) module 17.

As shown in FIG. 3, each mechanism unit (various dispensing arms, reaction unit 9, etc.) in the measurement mechanism section 2 is controlled by a CPU 2a arranged in the measurement mechanism section 2. The sample transport section 3 is also configured to be controlled by the CPU 2a. Furthermore, the measurement mechanism section 2 includes a storage unit 2b. The storage unit 2b stores control programs that cause the CPU 2a to execute the operation control of each mechanism unit of the measurement mechanism section 2. The CPU 2a is configured to perform the reagent information reading process and the reagent aspirating/reagent aspirating/reagent information writing process described below based on the control program.

As shown in FIG. 2, the cuvette supplying unit 10 is configured to accommodate a plurality of cuvettes (not shown), and sequentially supplies cuvettes one at a time to a sample discharging position by the sample dispensing arm 5.

The R1 reagent dispensing arm 6 aspirates the R1 reagent installed at the reagent installing unit 16, and dispenses (discharges) the aspirated R1 reagent into the cuvette mounted at the sample discharging position. The R1 reagent dispensing arm 6 also transfers the cuvette mounted at the sample discharging position to the reaction unit 9 by a catcher (not shown).

The pipette tip supplying unit 13 transports a plurality of inserted pipette tips (not shown) one at a time to the tip attaching position by the sample dispensing arm 5. A pipette tip is then attached to the distal end of the pipette of the sample dispensing arm 5 at the tip attaching position.

After the pipette tip is attached at the tip attaching position, the sample dispensing arm 5 aspirates the sample in the test tube transported to the sample aspirating position by the sample transport section 3, and dispenses (discharges) the sample to the cuvette at the sample discharging position dispensed with the R1 reagent by the R1 reagent dispensing arm 6.

The R2 reagent dispensing arm 7 aspirates the R2 reagent installed in the reagent installing unit 16. The R2 reagent dispensing arm 7 is configured to dispense (discharge) the aspirated R2 reagent into the cuvette containing the R1 reagent and the sample.

The reaction unit 9 is formed to a substantially circular ring shape so as to surround the periphery of the reagent installing unit 16 having a substantially circular shape in plan view. The reaction unit 9 is configured to rotate in a clockwise direction, and moves the cuvette held at a cuvette holding portion 9a to each processing position where various processes (dispensing of reagent, etc.) are carried out.

The primary BF separator 11 is configured to separate (B/F separate) the non-reactive R1 reagent (unnecessary component) and the magnetic particles from the specimen in the cuvette after the cuvette accommodating the sample, the R1 reagent, and the R2 reagent are transferred from the reaction unit 9 to the primary BF separator 11 by the catcher (not shown).

The R3 reagent dispensing arm 8 aspirates the R3 reagent installed in the reagent installing unit 16. The R3 reagent dispensing arm 8 is configured to dispense (discharge) the aspirated R3 reagent to the cuvette when the cuvette accommodating the specimen after the B/F separation by the primary BF separator 11 is transferred from the primary BF separator 11 to the reaction unit 9.

The secondary BF separator 12 is configured to separate the non-reactive R3 reagent (unnecessary component) and the magnetic particles from the specimen in the cuvette after the cuvette accommodating the specimen after the B/F separation by the primary BF separator 11 and the R3 reagent are transferred from the reaction unit 9 to the secondary BF separator 12 by the catcher (not shown).

The R4/R5 reagent supplying unit 15 is configured to dispense the R4 reagent and the R5 reagent to the cuvette accommodating the specimen after the B/F separation by the secondary BF separator 12 with a tube (not shown).

The detector 14 is arranged to measure the amount of antigen contained in a sample by detecting the light generated in the reaction process of the labeled antibody bound to the antigen of the sample performed with a predetermined process and the light emitting substrate with a photo multiplier tube.

As shown in FIG. 2, the reagent installing unit 16 includes a housing 16a (see FIG. 4) having a substantially cylindrical shape, a lid portion 16b arranged to cover the housing 16a from the upper side, and an open/close portion 16c, arranged in the lid portion 16b to be opened and closed when the user changes the R1 reagent container 24, the R3 reagent container 25, and the R2 reagent container 26, described below. An openable/closable window (not shown) is formed at the upper surface of the lid portion 16b corresponding to the aspirating position of the R1 reagent, the R2 reagent, and the R3 reagent. The R1 reagent, the R2 reagent, and the R3 reagent are respectively aspirated by the R1 reagent dispensing arm 6, the R2 reagent dispensing arm 7, and the R3 reagent dispensing arm 8 through the window. The housing 16a and the lid portion 16b configure the "accommodating section" of the present invention.

Figure 5:
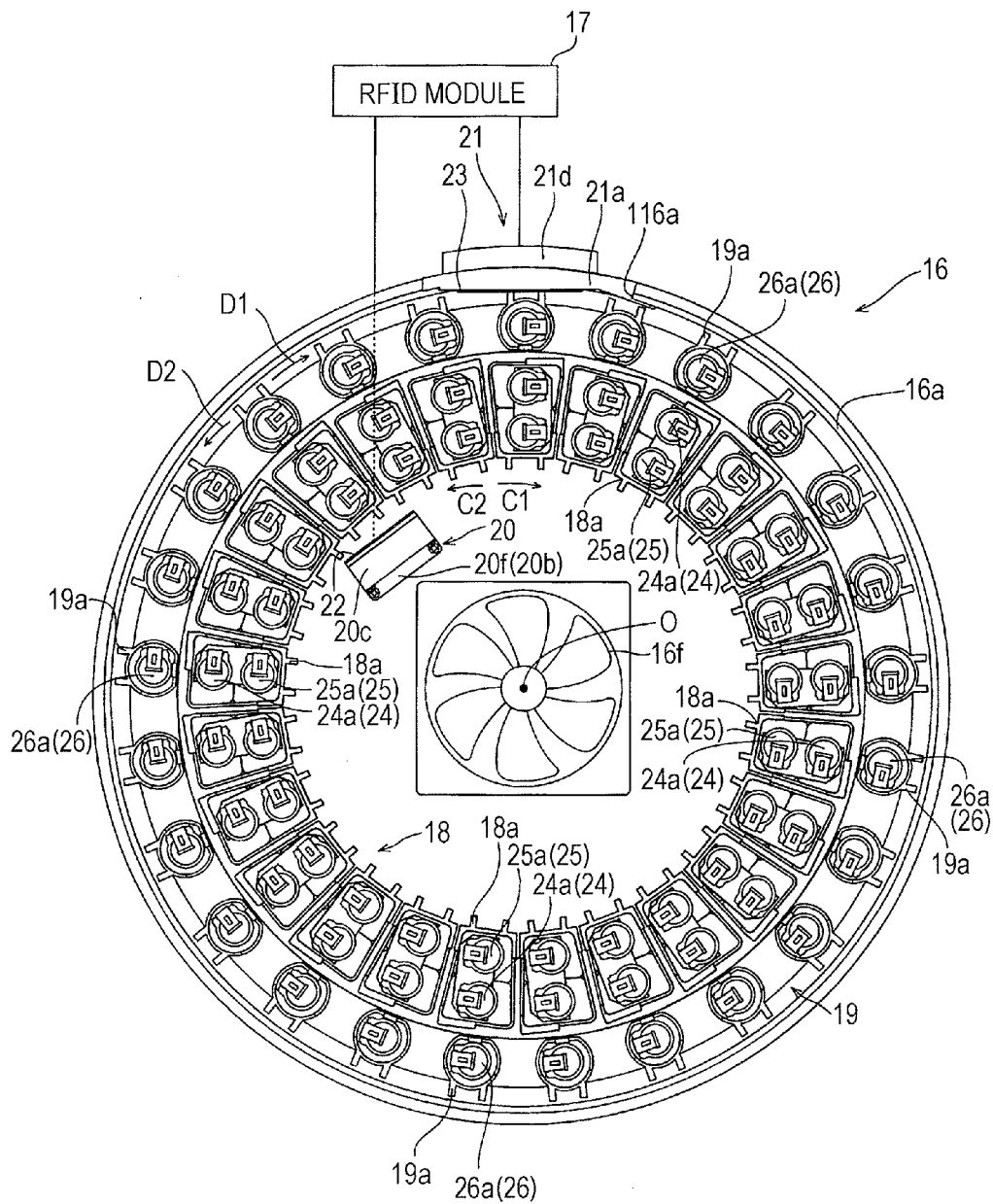
FIG. 5 is a plan view showing the interior of the reagent installing unit of the sample analyzer according to the first embodiment shown in FIG. 1.

As shown in FIG. 4 to FIG. 7, the housing 16a of the reagent installing unit 16 includes an R1/R3 installing portion 18, an R2 installing portion 19, an inner side antenna section 20, and an outer side antenna section 21. Specifically, as shown in FIG. 5, the R1/R3 installing portion 18, formed to a substantially circular ring shape having substantially the same center O as the center O of the housing 16a, and the R2 installing portion 19, formed to a substantially circular ring shape having substantially the same center O as the center of the housing 16a, are arranged inside the housing 16a in plan view. The R1/R3 installing portion 18 is arranged on the inner peripheral side (center O side) of the R2 installing portion 19. A cutout 116a is formed in the housing 16a by cutting one part of the side wall along the vertical direction (Z direction of FIG. 4).

The reagent installing unit 16 includes an inner side rotation drive portion 16d (see FIG. 3) for rotating the R1/R3 installing portion 18 in a horizontal direction (direction of the arrow C1 and in the direction of the arrow C2) with the center O as the center of rotation, and an outer side rotation drive portion 16e (see FIG. 3) for rotating the R2 installing portion 19 in the horizontal direction (direction of the arrow D1 and in the direction of the arrow D2) with the center O as the center of rotation. The inner side rotation drive portion 16d and the outer side rotation drive portion 16e are configured such that the drive is individually controlled by the CPU 2a. A fan 16f for cooling the R1 reagent, the R2 reagent, and the R3 reagent and a peltier element 16g (see FIG. 3) is arranged near the center O of the bottom of the housing 16a. This cooling may cause dew condensation in the reagent installing unit 16.

As shown in FIGS. 8 to 11, the inner side antenna section 20 includes an antenna substrate 20a, a substrate attachment portion 20b, and a lid member 20c. The substrate attachment portion 20b and the lid member 20c are both made of a resin that can transmit a radio wave.

Figure 11:
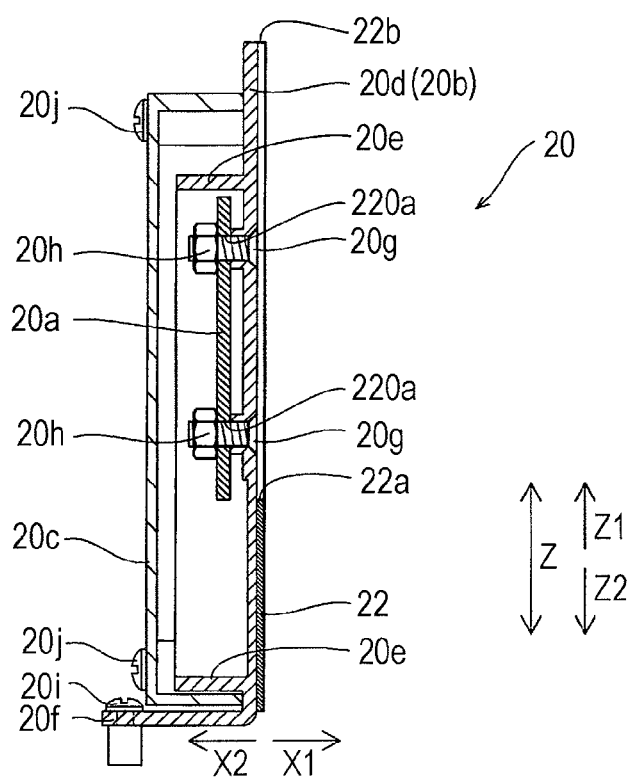
FIG. 11 is a cross-sectional view showing the inner side antenna section of the reagent installing unit taken along line 400-400 of FIG. 10.
Figure 12:
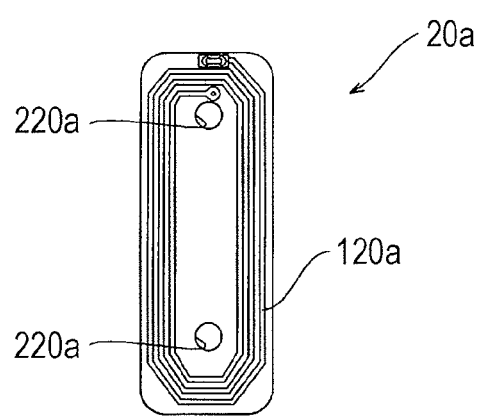
FIG. 12 is a plan view showing the antenna substrate of the inner side antenna section according to the first embodiment shown in FIG. 1.

As shown in FIG. 12, the antenna substrate 20a is configured to form a coil-shaped antenna section wiring 120a on a surface (see FIG. 11) on a side in the direction of the arrow X1 of the plate-shaped substrate, and is configured to transmit and receive the radio wave through the coil-shaped antenna section wiring 120a. A pair of screw holes 220a for receiving a pair of screws 20g (see FIG. 11) described below is formed near the central part of the antenna substrate 20a. The coil-shaped antenna section wiring 120a is formed to surround the pair of screw holes 220a.

Figure 6:
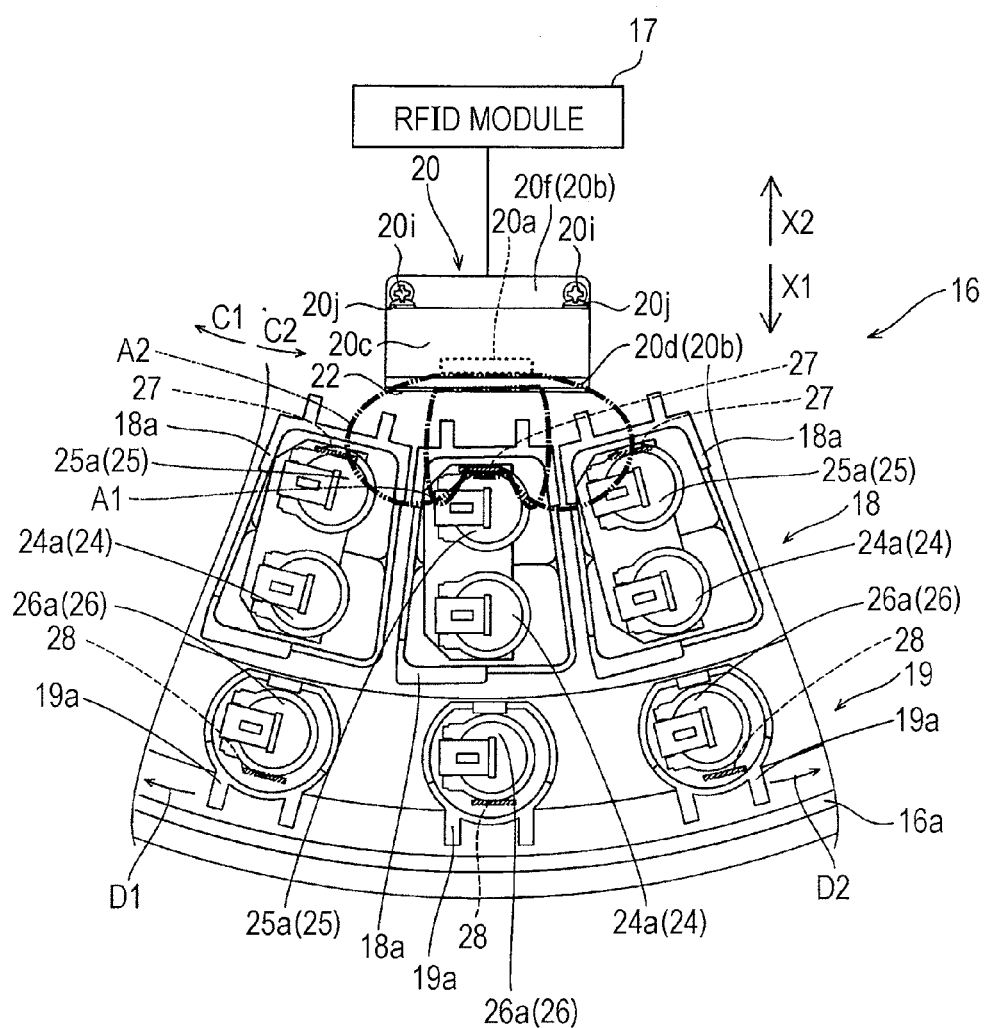
FIG. 6 is an enlarged plan view showing a state of reading the IC tag of an R3 reagent container of the reagent installing unit according to the first embodiment shown in FIG. 1.

As shown in FIG. 6, the antenna substrate 20a is arranged inside the substrate attachment portion 20b so that the surface on the side in the direction of the arrow X1 of the antenna substrate 20a faces the R1/R3 installing portion 18 side. The antenna substrate 20a is thus configured so as to be able to emit the read radio wave and the write radio wave towards the R1/R3 installing portion 18 side. The antenna substrate 20a is connected to an antenna switching substrate 17c (see FIG. 3), described below, of the RFID module 17.

Figure 10:
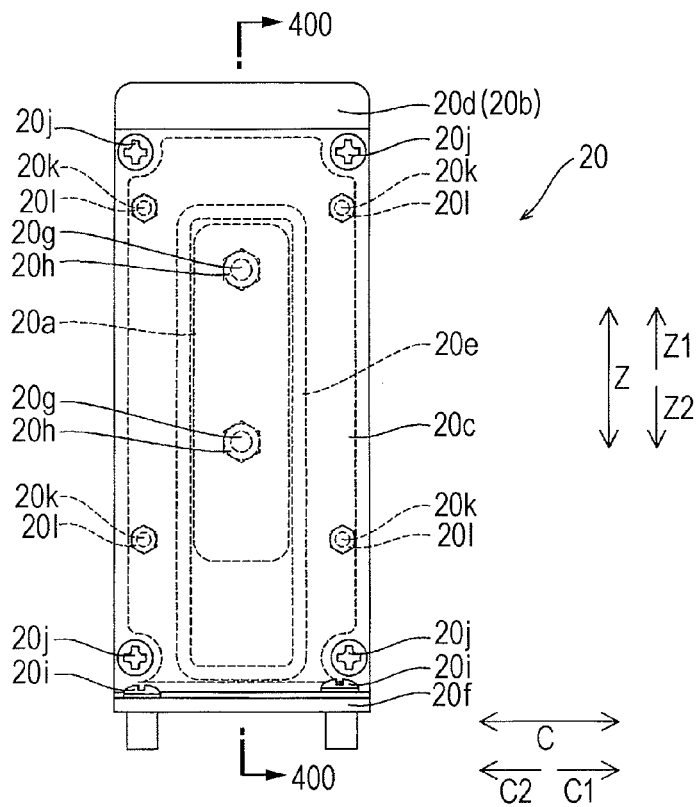
FIG. 10 is a rear view showing the inner side antenna section of the reagent installing unit according to the first embodiment shown in FIG. 1.

As shown in FIG. 10 and FIG. 11, the substrate attachment portion 20b is formed with a flat surface part 20d having a substantially square shape, a wall part 20e extending from the flat surface part 20d in the direction of the arrow X2 (see FIG. 11), and a fixed part 20f extending from the lower end on the side in the direction of the arrow Z2 of the flat surface part 20d in the direction of the arrow X2. The flat surface part 20d is formed to extend in a vertical direction (Z direction) on the side in the direction of the arrow X1 (see FIG. 11).

As shown in FIG. 10, the wall part 20e is formed to a substantially square frame shape in plan view.

As shown in FIG. 11, the antenna substrate 20a is fixed to the surface surrounded by the wall part 20e on the side in the direction of the arrow X2 of the flat surface part 20d by a pair of screws 20g and nuts 20h. The antenna substrate 20a is thereby fixed in a space surrounded by the wall parts 20e. The antenna substrate 20a is configured not to touch the flat surface part 20d other than at the two areas fixed with the screw. The coil-shaped antenna section wiring 120a (see FIG. 12) of the antenna substrate 20a thus can be suppressed from contacting the substrate attachment portion 20b. The fixed part 20f of the substrate attachment portion 20b is fixed to the bottom surface (see FIG. 6) of the housing 16a by a pair of screws 20i.

The lid member 20c has a recess shape depressed to the side in the direction of the arrow X2, and is arranged so that the recess shaped portion of the lid member 20c covers the space surrounded by the wall parts 20e from the direction of the arrow X2. The lid member 20c is fixed to the substrate attachment portion 20b with four screws 20j (see FIG. 10). The antenna substrate 20a, fixed in the space surrounded by the wall parts 20e, is thus covered by the substrate attachment portion 20b and the lid member 20c, and the space surrounded by the wall parts 20e is isolated from the outside. Since the substrate attachment portion 20b and the lid member 20c are both made of resin, the read radio wave and the write radio wave emitted from the antenna substrate 20a towards the R1/R3 installing portion 18 side (direction of the arrow X1) and the response radio wave emitted from the IC tag 27 described below are transmitted through the substrate attachment portion 20b and the lid member 20c and reach the R1/R3 installing portion 18 and the antenna substrate 20a even if the antenna substrate 20a is covered by the substrate attachment portion 20b and the lid member 20c.

Figure 8:
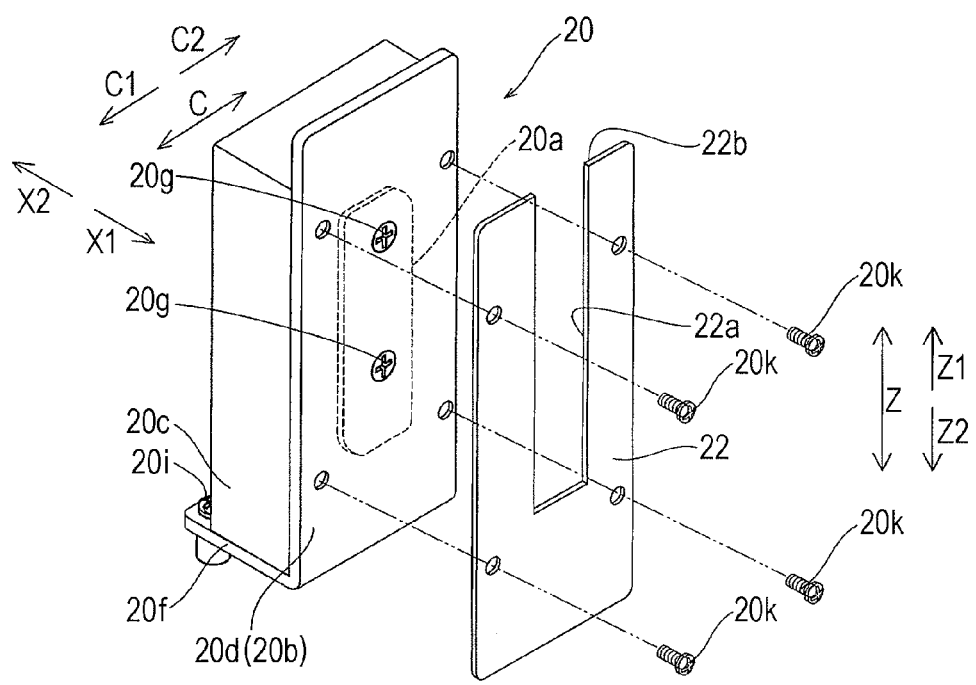
FIG. 8 is a perspective view showing an inner side antenna section of the reagent installing unit according to the first embodiment shown in FIG. 1.

In the first embodiment, a flat plate-shaped metal plate 22 is attached to the surface on a side in the direction of the arrow X1 of the inner side antenna section 20, as shown in FIG. 8. The metal plate 22 is fixed at four areas of the flat surface part 20d by four screws 20k and nuts 20l (see FIG. 10). The flat plate-shaped metal plate 22 is thereby attached closely to the flat surface part 20d of the substrate attachment portion 20b.

Figure 9:
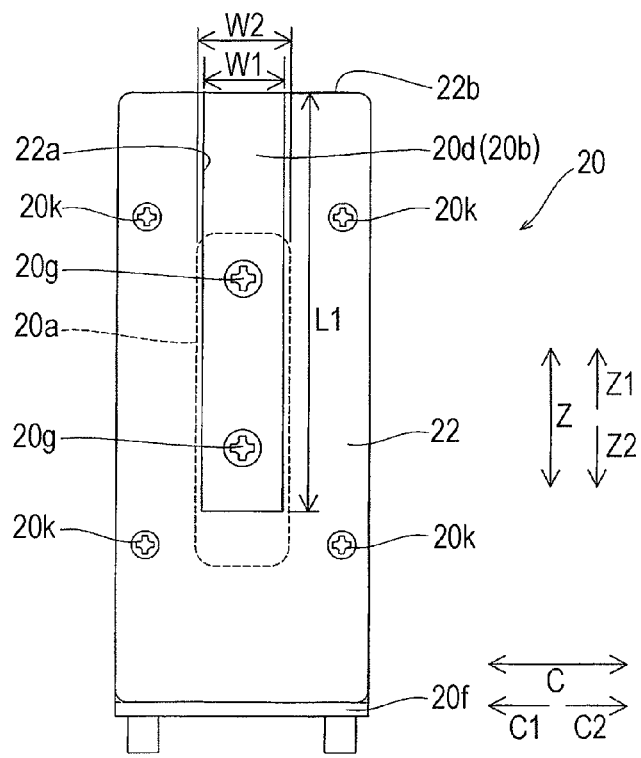
FIG. 9 is a front view showing the inner side antenna section of the reagent installing unit according to the first embodiment shown in FIG. 1.

The metal plate 22 is made of an aluminum plate material capable of absorbing the radio waves (read radio wave, write radio wave, and response wave). As shown in FIG. 9, the metal plate 22 extends in the vertical direction (Z direction) and is formed to a substantially square shape, similar to the flat surface part 20d.

In the first embodiment, the cutout 22a is formed at substantially the middle in the horizontal direction (C direction) of the metal plate 22. The cutout 22a is formed by cutting about ⅔ of the entire length in the Z direction of the metal plate 22 from the outer end 22b in the direction of the arrow Z1 of the metal plate 22 to a substantially square shape along the vertical direction (Z direction). The outer end 22b on the vertically upper side (side in the direction of the arrow Z1) of the metal plate 22 is thus separated by the cutout 22a. The length L1 in the vertical direction (Z direction) of the cutout 22a is configured to be greater than the width W1 in the horizontal direction (C direction) of the cutout 22a.

As shown in FIG. 6, the metal plate 22 is arranged in a region between the inner side antenna section 20 and the R3 reagent container 25 of the R1/R3 installing portion 18. The antenna substrate 20a is configured to emit the read radio wave and the write radio wave towards the R1/R3 installing position 18 side (direction of the arrow X1) through the cutout 22a (see FIG. 8) cut in the vertical direction (Z direction) of the metal plate 22, where the read radio wave and the write radio wave of the antenna substrate 20a that do not pass the cutout 22a are absorbed by the metal plate 22. Furthermore, the width W1 (see FIG. 9) in the horizontal direction (C direction) of the cutout 22a is slightly smaller than the width W2 (see FIG. 9) in the horizontal direction of the antenna substrate 20a. Range A1 is a range in the horizontal direction of the read radio waves and the write radio waves emitted from the antenna substrate 20a (chain dashed line). If the metal plate 22 is not provided, the range in the horizontal direction of the read radio waves and the write radio waves emitted from the antenna substrate 20a is range A2 (chain double dashed line) which is greater than the range A1. In other words, the metal plate 22 limits the reading range and the writing range by the inner side antenna section 20 (antenna substrate 20a).

As shown in FIG. 13 to FIG. 16, outer side antenna section 21 includes a lock portion 21a, an antenna substrate 21b, a substrate attachment portion 21c, and a lid member 21d.

The lock portion 21a, the substrate attachment portion 21c and the lid member 21d are all made of resin that can transmit a radio wave.

Figure 7:
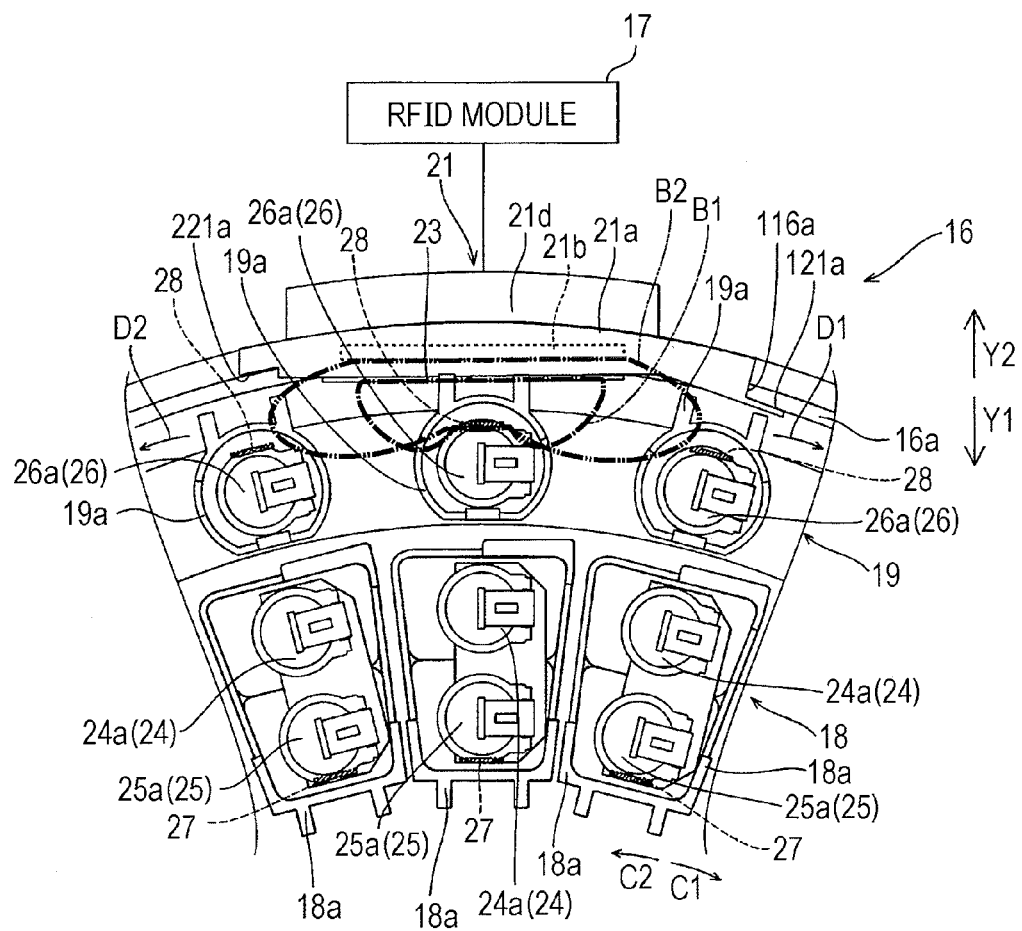
FIG. 7 is an enlarged plan view showing a state of reading the IC tag of an R2 reagent container of the reagent installing unit according to the first embodiment shown in FIG. 1.

As shown in FIG. 7, a step difference 121a is formed towards the inner side (direction of the arrow Y1) at the end one of a side (a side in the direction of the arrow D1) in the horizontal direction of the lock portion 21a. A step difference 221a is formed towards the outer side (side in the direction of the arrow Y2) at the end on the other side (the side in the direction of the arrow D2) in the horizontal direction of the lock portion 21a. Thus, when the lock portion 21a is locked to the cutout 116a of the housing 16a, the inner side surface of the housing 16a and the step difference 121a face each other on the side in the direction of the arrow D1, and the outer side surface of the housing 16a and the step difference 221a face each other on the side in the direction of the arrow D2. As a result, the lock portion 21a is configured to lock with the housing 16a so as to sandwich the housing 16a from the inner side and the outer side.

Figure 17:
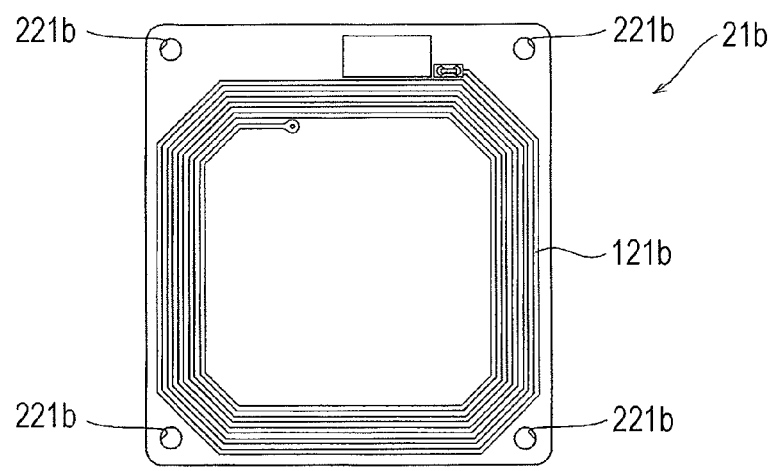
FIG. 17 is a plan view showing the antenna substrate of the outer side antenna section according to the first embodiment shown in FIG. 1.

As shown in FIG. 17, the antenna substrate 21b is formed by a coil-shaped antenna section wiring 121b on the surface (see FIG. 12) on the side in the direction of the arrow Y1 of the plate-shaped substrate, and is configured to transmit and receive the radio waves through the coil-shaped antenna section wiring 121b. Four screw holes 221b for receiving four screws 21h (see FIG. 15) described below are formed near the four corners of the antenna substrate 21b.

The coil-shaped antenna section wiring 121b is formed on the inner side of the screw holes 221b.

As shown in FIG. 7, the antenna substrate 21b is arranged inside the substrate attachment portion 21c so that the surface on the side in the direction of the arrow Y1 of the antenna substrate 21b faces the R2 installing portion 19 side.

The antenna substrate 21b is thus configured so as to be able to emit the read radio wave and the write radio wave towards the R2 installing portion 19 side. The antenna substrate 21b is connected to the antenna switching substrate 17c (see FIG. 3), described below, of the RFID module 17.

Figure 13:
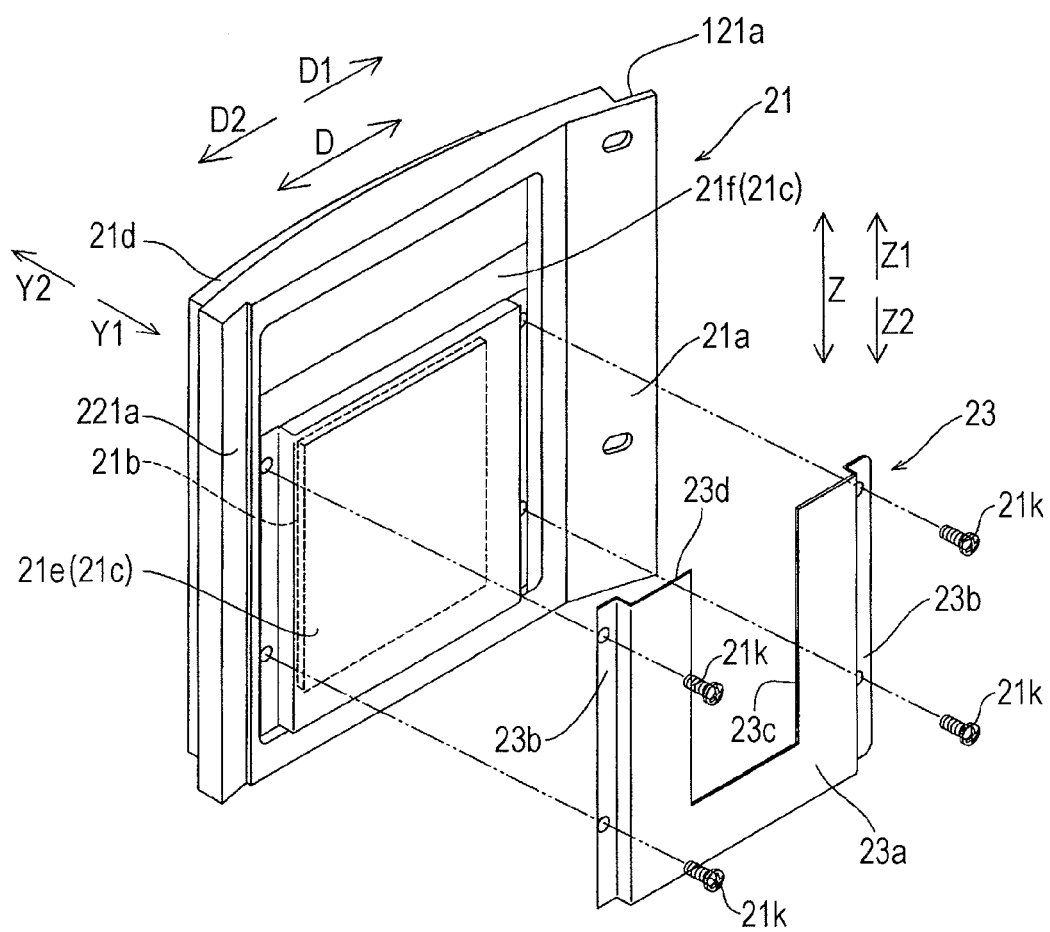
FIG. 13 is a perspective view showing the outer side antenna section of the reagent installing unit according to the first embodiment shown in FIG. 1.
Figure 16:
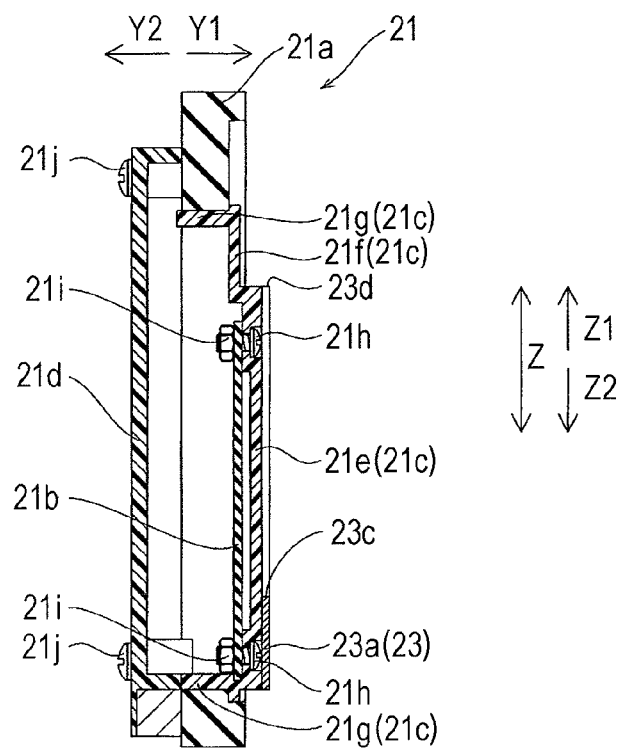
FIG. 16 is a cross-sectional view showing the outer side antenna section of the reagent installing unit taken along line 500-500 of FIG. 15.

As shown in FIG. 13 and FIG. 16, the substrate attachment portion 21c is formed with a flat surface part 21e having a substantially square shape, a step difference part 21f formed towards the side in the direction of the arrow Y2 (see FIG. 16) so as to surround the flat surface part 21e, and a wall part 21g extending from the periphery of the step difference part 21f in the direction of the arrow Y2. The flat surface part 21e is formed to extend in the vertical direction (Z direction) on the side in the direction of the arrow Y1 (see FIG. 16), and the portion other than the portion to be attached with the antenna substrate 21b of the surface on the side in the direction of the arrow Y2 is depressed to the side in the direction of the arrow Y1.

Figure 15:
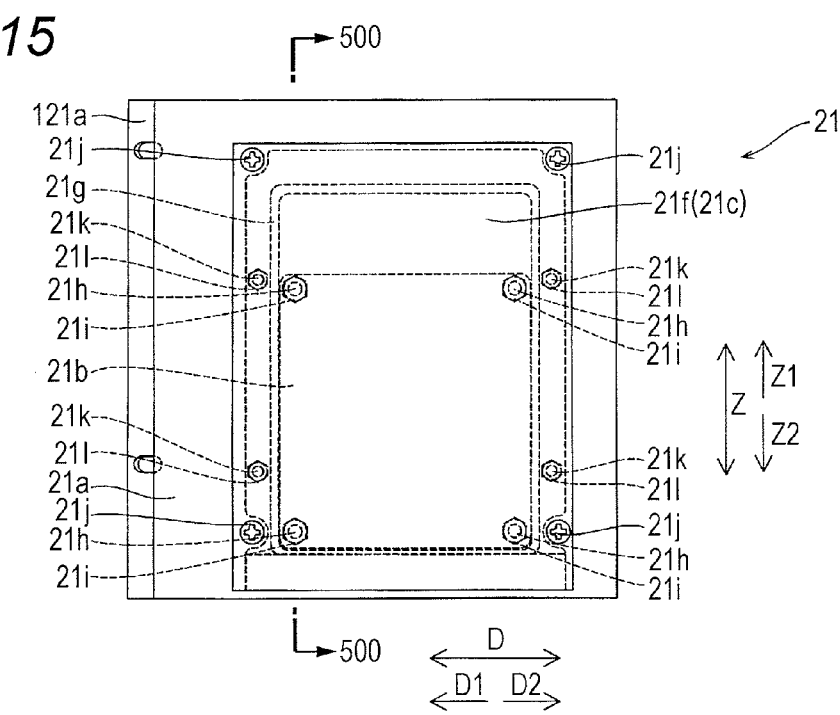
FIG. 15 is a rear view showing the outer side antenna section of the reagent installing unit according to the first embodiment shown in FIG. 1.

As shown in FIG. 15 and FIG. 16, the antenna substrate 21b is fixed to the surface surrounded by the wall part 21g on the side in the direction of the arrow Y2 of the flat surface part 21e by four screws 21h and nuts 21i. The antenna substrate 21b is thereby fixed in a space surrounded by the wall parts 21g. The antenna substrate 21b is configured so as not to contact the flat surface part 21e (depressed portion) other than the portion to be attached to the flat surface part 21e when attached to the flat surface part 21e.
The coil-shaped antenna section wiring 121b (see FIG. 17) is formed on the inner side of the screw holes 221b of the antenna substrate 21b, and thus can be suppressed from contacting the substrate attachment portion 21c.

As shown in FIG. 16, the lid member 21d has a recess shape depressed to the side in the direction of the arrow Y2, and is arranged so that the recess shaped portion of the lid member 21d covers the space surrounded by the wall parts 21g from the direction of the arrow Y2. The lid member 21d is fixed to the lock portion 21a with four screws 21j (see FIG. 15). The antenna substrate 21b which is fixed in the space surrounded by the wall parts 21g is thus covered by the substrate attachment portion 21c and the lid member 21d, and the space surrounded by the wall parts 21g is isolated from the outside. Since the substrate attachment portion 21c is made of resin, the read radio waves and the write radio waves emitted from the antenna substrate 21b towards the R2 installing portion 19 side (direction of the arrow Y1) and the response radio wave emitted from the IC tag 28 described below transmit through the substrate attachment portion 21c and the lid member 21d and reach the R2 installing portion 19 and the antenna substrate 21b even if the antenna substrate 21b is covered by the substrate attachment portion 21c and the lid member 21d.

As shown in FIG. 13, in the first embodiment, a metal plate 23 is attached to the surface on the side in the direction of the arrow Y1 of the outer side antenna section 21. Specifically, the metal plate 23 is configured by a flat surface part 23a, and a step difference part 23b formed at both ends in the horizontal direction (D direction) of the flat surface part 23a and having a thickness which is substantially the same as the flat surface part 23a. The step difference part 23b of the metal plate 23 is fixed at four areas of the step difference part 21f of the outer side antenna section 21 by four screws 21k and nuts 21l (see FIG. 15). The metal plate 23 is closely attached to the flat surface part 21e of the substrate attachment portion 21c and the step difference part 23b is closely attached to the step difference part 21f of the substrate attachment portion 21c. The metal plate 23 is made of an aluminum plate material capable of absorbing the radio waves (read radio wave, write radio wave, and response wave).

Figure 14:
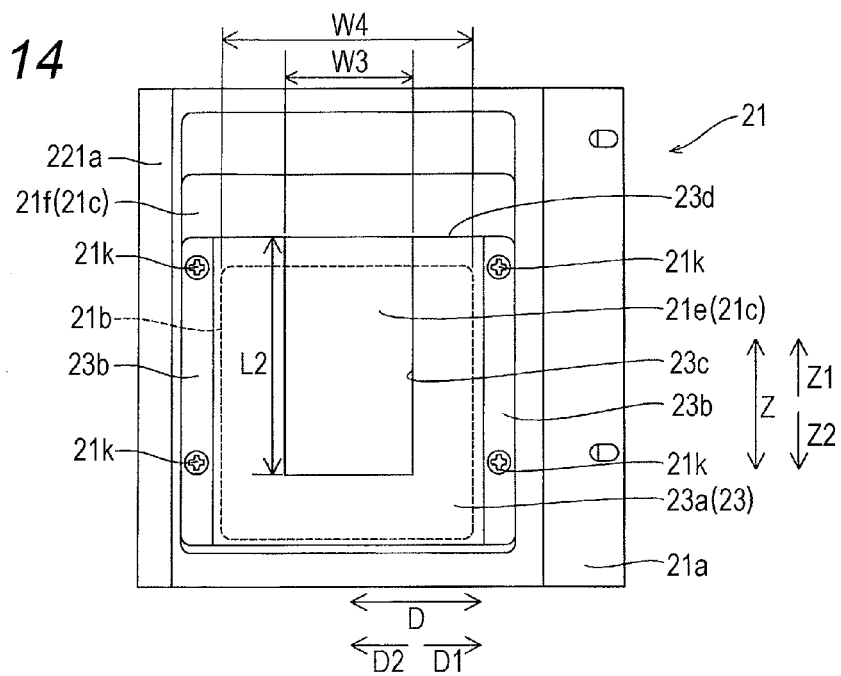
FIG. 14 is a front view showing the outer side antenna section of the reagent installing unit according to the first embodiment shown in FIG. 1.

As shown in FIG. 14, a cutout 23c is formed at substantially the middle in the horizontal direction (D direction) of the flat surface part 23a of the metal plate 23 in the first embodiment. The cutout 23c is formed by cutting about ¾ of the entire length in the Z direction of the flat surface part 23a (metal plate 23) from the outer end 23d in the direction of the arrow Z1 of the flat surface part 23a to a substantially square shape along the vertical direction (Z direction). The outer end 23d on the side in the direction of the arrow Z1 of the metal plate 23 is thus separated by the cutout 23c. The length L2 in the vertical direction (Z direction) of the cutout 23c is configured to be greater than the width W3 in the horizontal direction (D direction) of the cutout 23c.

As shown in FIG. 7, the metal plate 23 is arranged in a region between the outer side antenna section 21 and the R2 reagent container 26 of the R2 installing portion 19. The antenna substrate 21b is configured to emit the read radio waves and the write radio waves towards the R2 installing position 19 side (direction of the arrow Y1) through the cutout 23c (see FIG. 13) cut in the vertical direction (Z direction) of the metal plate 23, where the read radio waves and the write radio waves of the antenna substrate 21b that do not pass the cutout 23c are absorbed by the flat surface plate 23a of the metal plate 23. Furthermore, the width W3 (see FIG. 14) in the horizontal direction of the cutout 23c is slightly smaller than the width W4 (see FIG. 14) in the horizontal direction of the antenna substrate 21b. Range B1 is a range in the horizontal direction of the read radio waves and the write radio waves emitted from the antenna substrate (chain dashed line). If the metal plate 23 is not provided, the range in the horizontal direction of the read radio waves and the write radio waves emitted from the antenna substrate 21b is range B2 (chain double dashed line) which is greater than the range B1. In other words, the metal plate 23 limits the reading range and the writing range by the outer side antenna section 21 (antenna substrate 21b).

As shown in FIG. 5, the R1/R3 installing portion 18 includes twenty five R1/R3 holding members 18a (reagent container holders), which are made of resin capable of transmitting the radio waves, arranged at an equal angle (about 14.4 degrees). Each R1/R3 holding member 18a holds the R1 reagent containers 24 for accommodating the R1 reagent (first reagent) containing the capture antibody, and the R3 reagent containers 25 for accommodating the R3 reagent containing the labeled body. The R1/R3 holding member 18a is configured such that the R1 reagent containers 24 are held on the outer peripheral side (R2 installing portion 19 side) and the R3 reagent containers 25 are held on the inner peripheral side (center O side).

The R2 installing portion 19 includes twenty five R2 holding members 19a, which are made of resin capable of transmitting the radio waves and which are arranged at an equal angle (about 14.4 degrees). Each R2 holding member 19a holds the R2 reagent containers 26 for accommodating the R2 reagent (second reagent) containing the magnetic particles. The R1 reagent containers 24, the R3 reagent containers 25, and the R2 reagent containers 26 are configured to be installed and changed by the user.

Figure 18:
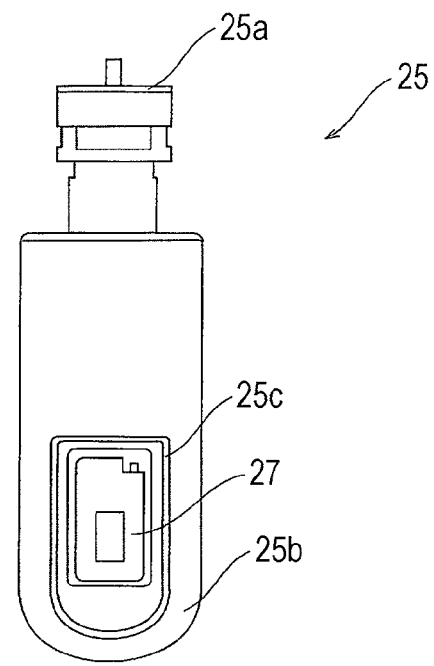
FIG. 18 is a side view showing the R3 reagent container of the reagent installing unit according to the first embodiment shown in FIG. 1.
Figure 19:
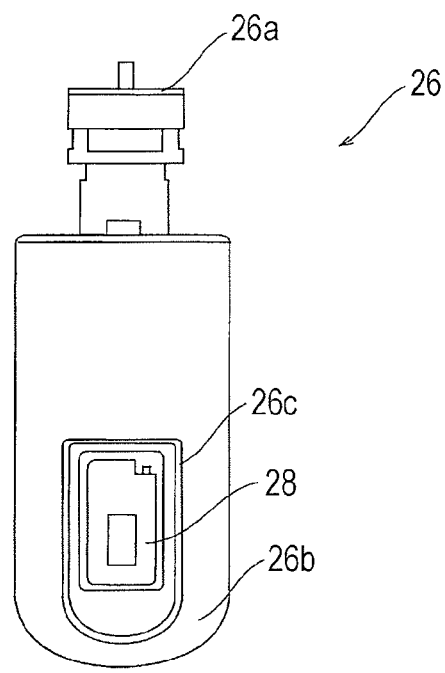
FIG. 19 is a side view showing the R2 reagent container of the reagent installing unit according to the first embodiment shown in FIG. 1.

As shown in FIG. 18, the R3 reagent container 25 is formed with a lid 25a that opens and closes when aspirating the R3 reagent, and with a reagent accommodating portion 25b for accommodating the R3 reagent.
As shown in FIG. 19, the R2 reagent container 26 is formed with a lid 26a that opens and closes when aspirating the R2 reagent, and with a reagent accommodating portion 26b for accommodating the R2 reagent. As shown in FIG. 6 and FIG. 7, the R1 reagent container 24 has substantially a similar shape as the R3 reagent container 25, and the R1 reagent container 24 is formed with a lid 24a that opens and closes when aspirating the R1 reagent, and a reagent accommodating portion (not shown) for accommodating the R1 reagent. The lids 24a and 25a are configured to open and close with the rotation of the R1/R3 installing portion 18, and the lid 26a is configured to open and close with the rotation of the R2 installing portion 19.

As shown in FIG. 18, an IC tag attachment portion 25c, to which the IC tag 27 is attached, is formed on the side surface arranged on the inner peripheral side (side in the direction of the arrow X2 in FIG. 6) of the reagent accommodating portion 25b of the R3 reagent container 25. As shown in FIG. 19, an IC tag attachment portion 26c, to which the IC tag 28 is attached, is formed on the side surface arranged on the outer peripheral side (side in the direction of the arrow Y2 in FIG. 7) of the reagent accommodating portion 26b of the R2 reagent container 26. As shown in FIG. 6, the IC tag 27 of the R3 reagent container 25 is attached so as to face the inner peripheral side (side in the direction of the arrow X2) of the reagent installing unit 16 when the R3 reagent container 25 is arranged in the R1/R3 installing portion 18. As shown in FIG. 7, the IC tag 28 of the R2 reagent container 26 is attached so as to face the outer peripheral side (side in the direction of the arrow Y2) of the reagent installing unit 16 when the R2 reagent container 26 is arranged in the R2 installing portion 19. The IC tag is not attached to the side surface of the R1 reagent container 24, which is different from the R3 reagent container 25.

The IC tag 27 is recorded with the reagent information of the R3 reagent of the R3 reagent container 25, and the reagent information of the R1 reagent of the R1 reagent container 24 held in the R1/R3 holding member 18a common with the R3 reagent container 25. The IC tag 28 is recorded with the reagent information of the R2 reagent of the R2 reagent container 26.

Specifically, the IC tags 27 and 28 are recorded with reagent information such as the measurement item, the reagent type (type specifying information), the lot number, the serial number, the storage period, and the filled amount, the remaining amount and the expiration date for use.

As shown in FIG. 6, the IC tag 27 of the R3 reagent container 25 is configured so that read and write are carried out at the front surface position (position facing) of the inner side antenna section 20. Similarly, as shown in FIG. 7, the IC tag 28 of the R2 reagent container 26 is configured so that read and write are carried out at the front surface position of the outer side antenna section 21. In this case, the IC tags 27 and 28 are configured to emit the response radio wave containing the reagent information recorded in the IC tags 27 and 28 based on the read radio wave emitted from the inner side antenna section 20 and the outer side antenna section 21. The IC tags 27 and 28 are configured to rewrite the recorded reagent information to the new reagent information contained in the write radio wave based on the write radio wave emitted from the inner side antenna section 20 and the outer side antenna section 21.

The interval between the adjacent R1/R3 holding members 18a and the range A1 are set so that read and write are carried out on a specific IC tag 27, and read and write are not carried out on another IC tag 27. Similarly, the interval between the adjacent R2 holding members 19a and the range B1 are set so that read and write are carried out on a specific IC tag 28, and read and write are not carried out on another IC tag 28.

As shown in FIG. 3, the storage unit 4d of the control device 4 individually stores the respective reagent information of twenty five R1 reagent containers 24, twenty five R3 reagent containers 25, and twenty five R2 reagent containers 26 apart from the IC tags 27 and 28. The storage unit 4d stores the respective initial position of the twenty five R1 reagent containers 24, the twenty five R3 reagent containers 25, and the twenty five R2 reagent containers 26, and the rotation angle from the respective initial position of the R1/R3 installing portion 18 and the R2 installing portion 19 as positional information. The storage unit 4d thus stores the positional information and the reagent information of twenty five R1 reagent containers 24, the 25 R3 reagent containers 25, and the 25 R2 reagent containers 26 in a corresponding state.

When the power supply (not shown) of the sample analyzer 1 is turned ON, the IC tags (IC tags 27 and 28) of all the reagent containers (R3 reagent container 25 and R2 reagent container 26) installed in the reagent installing unit 16 are read, and the positional information and the reagent information of each reagent container are acquired by the CPU 2a. If the reagent information is stored in the storage unit 4d, the CPU 4a of the control device 4 updates the reagent information stored in the storage unit 4d to the reagent information acquired from the IC tag when the power supply is turned ON. Thus, even if the R1 reagent container 24, the R3 reagent container 25, and the R2 reagent container 26 are respectively changed to a new R1 reagent container 24, R3 reagent container 25, and R2 reagent container 26 while the power supply of the sample analyzer 1 is turned OFF, the reagent information stored in the storage unit 4d of the control device 4 can be updated to the information of the reagent currently installed at the reagent installing unit 16.

As shown in FIG. 2, the RFID module 17 is arranged exterior to the reagent installing unit 16, and includes a reader/writer substrate 17a, an interface substrate 17b for intermediating the reader/writer substrate 17a and the CPU 2, and an antenna switching substrate 17c, as shown in FIG. 3.

The reader/writer substrate 17a is configured to emit the read radio wave and the write radio wave having the frequency band of about 13.56 MHz from the inner side antenna section 20 (outer side antenna section 21) based on the instruction from the CPU 2a. The reader/writer substrate 17a is also configured to acquire the reagent information from the response radio wave emitted from the IC tags 27 and 28 in response to the read radio wave and received by the inner side antenna section 20 and the outer side antenna section 21, and to output the reagent information to the CPU 2a.

The antenna switching substrate 17c switches to transmit the read radio wave and the write radio wave using either the inner side antenna section 20 or the outer side antenna section 21, and switches to receive the response radio wave using either the inner side antenna section 20 or the outer side antenna section 21 based on the instruction from the reader/writer substrate 17a.

The measurement operation of the sample analyzer 1 (measurement mechanism section 2) according to the first embodiment of the present invention will now be described with reference to FIG. 3 and FIG. 20.

First, when the power supply of the measurement mechanism section 2 is turned ON, the CPU 2a of the measurement mechanism section 2 initializes (initialization of the program) of the CPU 2a in step S1 and executes an initialization process such as operation check of each unit of the measurement mechanism section 2.

Thereafter, the reagent information reading process is performed in step S2. The reagent information reading process is described in detail below.

In step S3, whether a measurement instruction by the user is made is determined by the CPU 2a. The measurement instruction by the user is transmitted to the CPU 2a through the control device 4 (see FIG. 3). If it is determined that the measurement instruction by the user is not made, the process proceeds to step S6.

If it is determined that the measurement instruction by the user is made in step S3, the reagent aspirating/reagent information writing process is carried out by the CPU 2a in step S4. The reagent aspirating/reagent information writing process is described in detail below.

Subsequently, the sample is measured in the measurement mechanism section 2 in step S5. In step S6, whether the instruction to shut down by the user is made is determined by the CPU 2a. The process returns to step S3 if it is determined that the instruction of shutdown is not made. If it is determined that the instruction of shutdown is made, the shutdown of the measurement mechanism section 2 is carried out by the CPU 2a in step S7. The measurement operation of the CPU 2a of the measurement mechanism section 2 is terminated in such manner.

Figure 20:
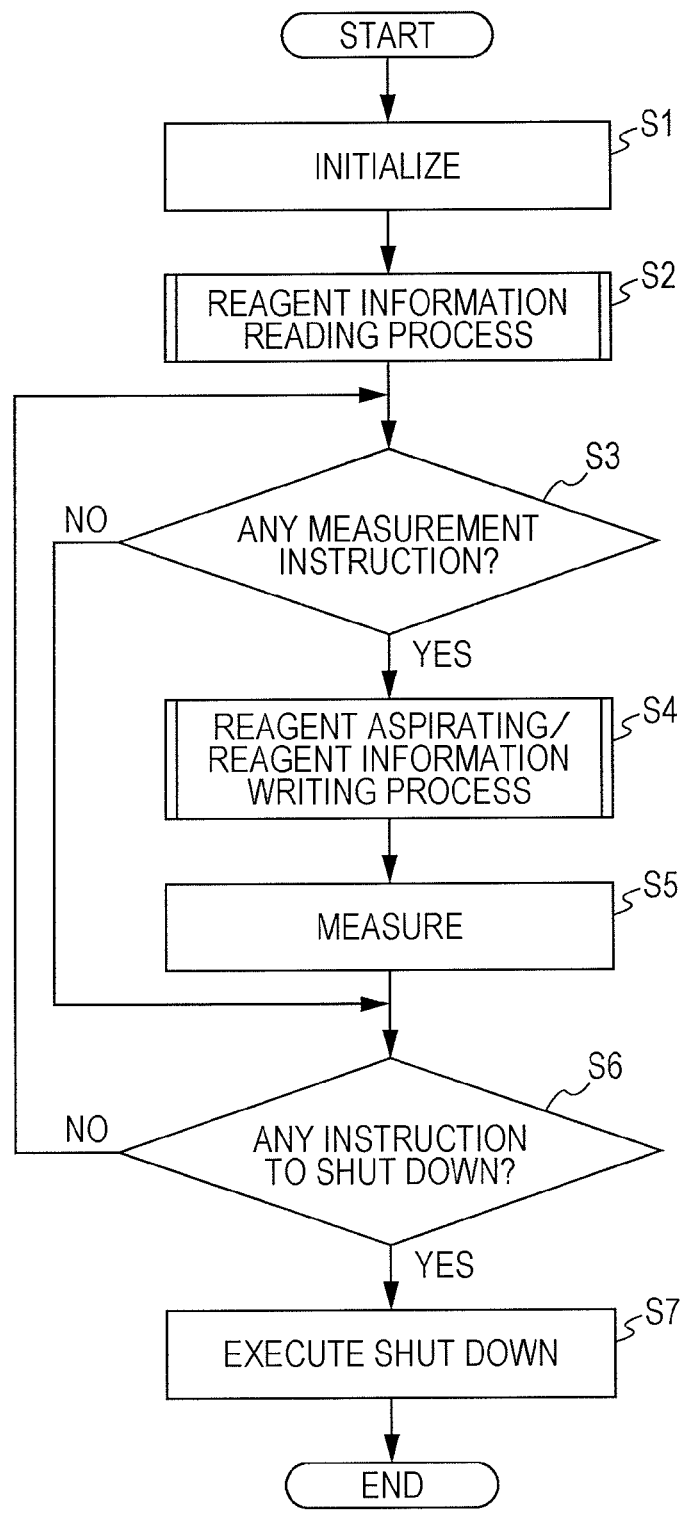
FIG. 20 is a flowchart showing the measurement operation of the sample analyzer according to the first embodiment shown in FIG. 1.
Figure 21:
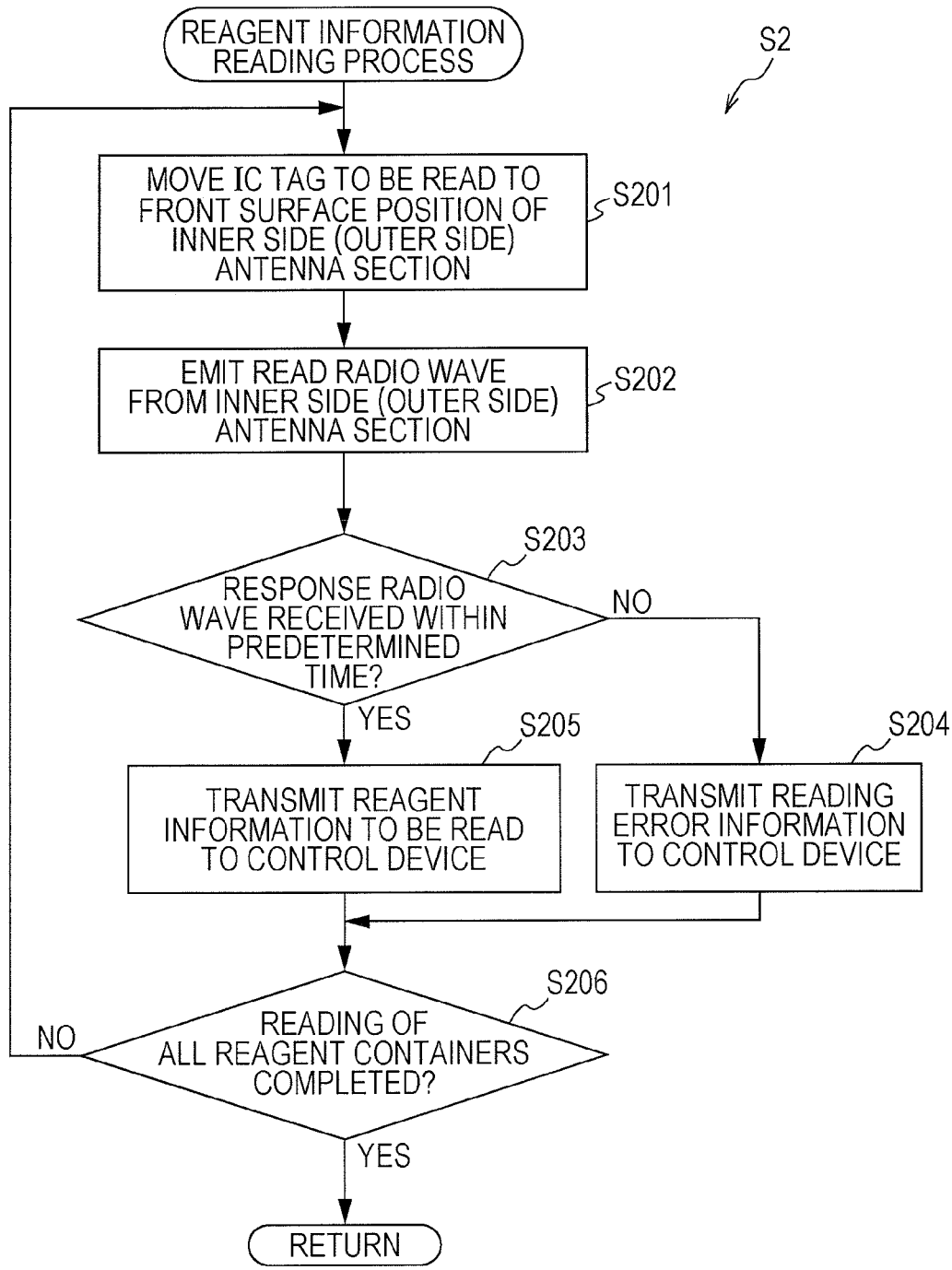
FIG. 21 is a flowchart showing a reagent information reading process of the sample analyzer according to the first embodiment shown in FIG. 1.

With reference to FIG. 6, FIG. 7, and FIG. 21, the reagent information reading process of the sample analyzer 1 according to the first embodiment of the present invention shown in step S2 of FIG. 20 is described below in detail.

First, in step S201, the R1/R3 installing portion 18 (R2 installing portion 19) is rotated in the direction of the arrow C1 (D1) or the direction of the arrow C2 (D2) (see FIG. 6 and FIG. 7) so that the IC tag 27 (28) to be read is positioned at the position facing the inner side antenna section 20 (outer side antenna section 21) by the CPU 2a. In step S202, the read radio wave is emitted from the inner side antenna section 20 (outer side antenna section 21) to the IC tag 27 (28) to be read by the CPU 2a.

Thereafter, in step S203, whether the response radio wave emitted from the IC tag 27 (28) in correspondence with the read radio wave is received within a predetermined time by the inner side antenna section 20 (outer side antenna section 21) is determined by the CPU 2a. In other words, whether the reagent information acquired by the reader/writer substrate 17a of the RFID module 17 based on the response radio wave received from the inner side antenna section 20 (outer side antenna section 21) is output to the CPU 2a within a predetermined time is determined by the CPU 2a. If it is determined that the response radio wave is not received within the predetermined time by the inner side antenna section 20 (outer side antenna section 21), determination is made that the reading failed, and the reading error information is transmitted to the control device 4 by the CPU 2a in step S204. The notification that the reading of the reagent information (reagent information of the reagent container to be read) of the reagent container positioned at a predetermined position failed is displayed on the display unit 4b of the control device 4.
The process then proceeds to step S206.

If it is determined that the response wave is received within the predetermined time by the inner side antenna section 20 (outer side antenna section 21), the reagent information to be read contained in the response radio wave is transmitted to the control device 4 in step S205. In the control device 4, the reagent information of the storage unit 4d is updated based on the reagent information to be read received from the CPU 2a. The process then proceeds to step S206.

Lastly, in step S206, whether all the reading of 25 IC tags 27 and 25 IC tags 28 is completed is determined by the CPU 2a. If it is determined that the reading is not yet completed, the process returns to step S201, and the reading of a new IC tag is carried out. If it is determined that all the reading is carried out, the reagent information reading process is terminated, and the process proceeds to step S3 shown in FIG. 20.

Figure 22:
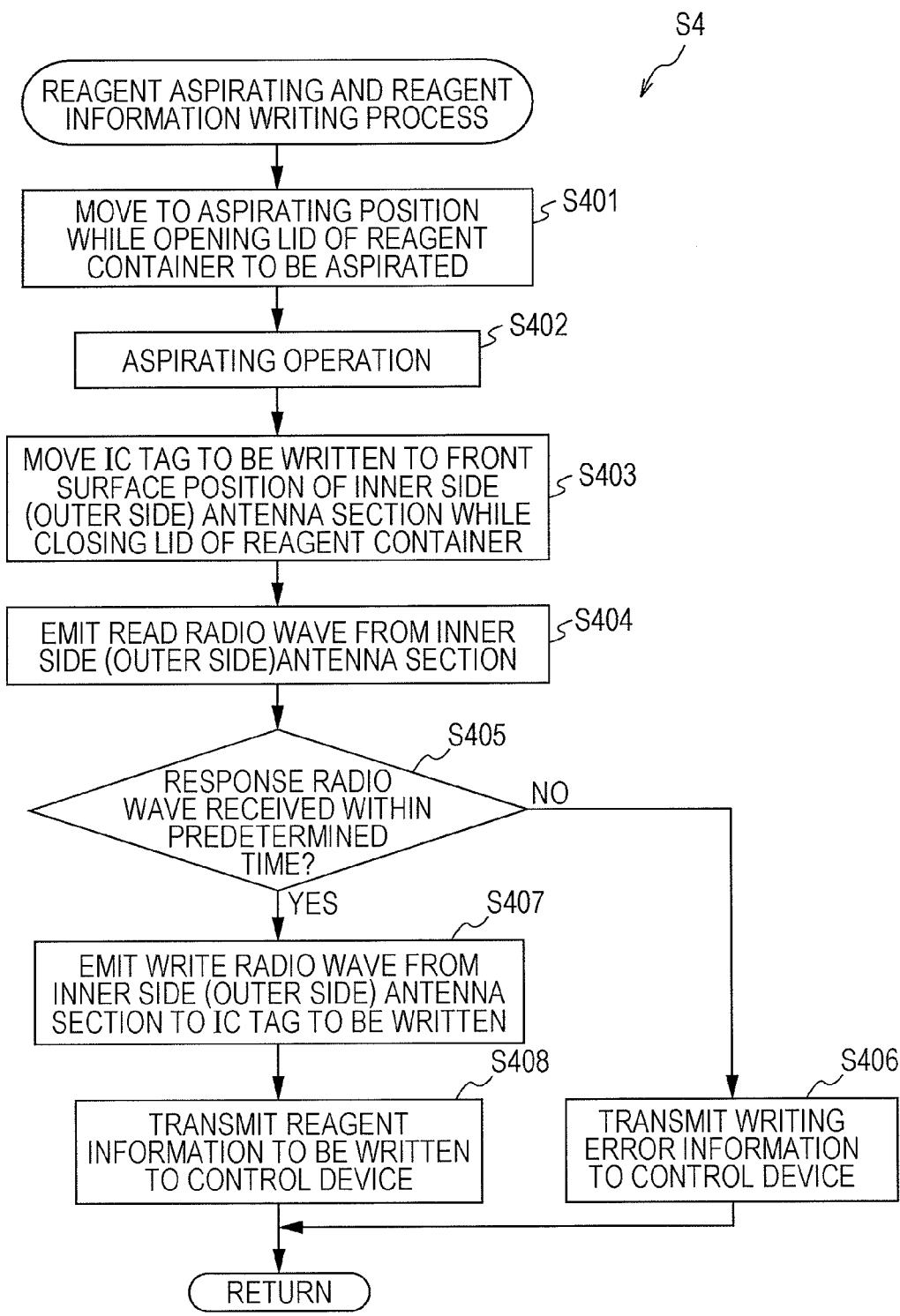
FIG. 22 is a flowchart showing a reagent aspirating and a reagent information writing process of the sample analyzer according to the first embodiment shown in FIG. 1.

With reference to FIG. 6, FIG. 7, and FIG. 22, the reagent aspirating and reagent information writing process of the sample analyzer 1 according to the first embodiment of the present invention shown in step S4 of FIG. 20 will now be described in detail.

First, in step S401, the R1/R3 installing portion 18 (R2 installing portion 19) is rotated in the direction of the arrow C1 (D1) or the direction of the arrow C2 (D2) (see FIG. 6 and FIG. 7) so that the R1 reagent container 24 or the R3 reagent container 25 (R2 reagent container 26) to be aspirated is positioned at the aspirating position where the R1 reagent or the R3 reagent (R2 reagent) is aspirated by the CPU 2a. In this case, the lid 24a of the R1 reagent container 24 or the lid 25a of the R3 reagent container 25 (lid 26a of the R2 reagent container 26) is opened with the rotation of the R1/R3 installing portion 18 (R2 installing portion 19).

In step S402, the R1 reagent or the R3 reagent (R2 reagent) is aspirated. Thereafter, in step S403, the R1/R3 installing portion 18 (R2 installing portion 19) is rotated in the direction of the arrow C1 (D1) or the direction of the arrow C2 (D2) so that the IC tag 27 (28) to be written by the CPU 2a is positioned at a position facing the inner side antenna section 20 (outer side antenna section 21). In this case, the lid 24a of the R1 reagent container 24 or the lid 25a of the R3 reagent container 25 (lid 26a of the R2 reagent container 26) is closed with the rotation of the R1/R3 installing portion 18 (R2 installing portion 19).

In step S404, the read radio wave is emitted from the inner side antenna section 20 (outer side antenna section 21) to the IC tag 27 (28) to be written by the CPU 2a. Thereafter, in step S405, whether the inner side antenna section 20 (outer side antenna section 21) received the response radio wave within a predetermined time is determined by the CPU 2a. If it is determined that the inner side antenna section 20 (outer side antenna section 21) did not receive the response radio wave within the predetermined time, the reading error information is transmitted to the control device 4 by the CPU 2a in step S406, and notification that the reagent information cannot be written to the IC tag to be written is displayed on the display unit 4b of the control device 4. The reagent aspirating and reagent information writing process is then terminated, and the process proceeds to step S5 shown in FIG. 20.

If it is determined that the inner side antenna section 20 (outer side antenna section 21) received the response radio wave within the predetermined time in step S405, the write radio wave including the remaining amount information and the like of the reagent is transmitted from the inner side antenna section 20 (outer side antenna section 21) to the IC tag 27 (28) to be written in step S407. In step S408, the same information as the reagent information written to the IC tag 27 (28) is transmitted to the control device 4 by the CPU 2a, and then the reagent aspirating and reagent information writing process is terminated, and the process proceeds to step S5 shown in FIG. 20. In the control device 4, the reagent information to be written is updated based on the reagent information transmitted from the CPU 2a.

In the first embodiment, the metal plate 22 is arranged between the inner side antenna section 20 and the R3 reagent container 25 of the R1/R3 installing portion 18, and the metal plate 23 is arranged between the outer side antenna section 21 and the R2 reagent container 26 of the R2 installing portion 19. The reagent information recorded on the IC tag that does not need to be subjected to reading of the reagent information thus can be suppressed from being mistakenly read by the inner side antenna section 20 and the outer side antenna section 21.
Therefore, the reagent information recorded on the IC tag that does not need to be subjected to reading can be suppressed from being mistakenly read without ensuring a large arrangement interval between the adjacent R3 reagent containers 25, and as a result, the immune analyzer 1 can be suppressed from enlarging. The reagent information recorded on a plurality of IC tags can be acquired in a shorter time by arranging the inner side antenna section 20 and the outer side antenna section 21.

Furthermore, in the first embodiment, the cutout 22a is formed at substantially the middle in the horizontal direction (C direction) of the metal plate 22, and the cutout 23c is formed at substantially the middle in the horizontal direction (D direction) of the metal plate 23. Therefore, unnecessary radio waves can be absorbed at the portions other than the cutouts 22a and 23c of the metal plates 22 and 23, so that the range of the radio wave emitted from the inner side antenna section 20 and the outer side antenna section 21 can be easily limited to the desired range.

In the first embodiment, the cutouts 22a and 23c are formed to extend up to the outer ends 22b and 23d on the side in the direction of the arrow Z1, so that the cutouts 22a and 23c are not surrounded by the metal plates 22 and 23, and the eddy current can be suppressed from generating at the metal plates 22 and 23. The output of the radio waves passing through the cutouts 22a and 23c thus can be easily suppressed from weakening.

In the first embodiment, the length L1 in the vertical direction of the cutout 22a of the metal plate 22 is configured to be greater than the width W1 in the horizontal direction, and the length L2 in the vertical direction of the cutout 23c of the metal plate 23 is configured to be greater than the width W3 in the horizontal direction. Therefore, when the R3 reagent containers 25 and the R2 reagent containers 26 are arranged adjacent to each other in the horizontal direction, the inner side antenna section 20 and the outer side antenna section 21 can be suppressed from mistakenly receiving the radio wave from the IC tag that does not need to be subjected to the reading of the reagent information, and the inner side antenna section 20 and the outer side antenna section 21 can be suppressed from mistakenly reaching the radio wave with respect to the IC tags 27 and 28 that do not need to be subjected to the writing of the reagent information.

In the first embodiment, the inner side rotation drive portion 16d for rotating the R1/R3 installing portion 18 in the direction of the arrow C1 and in the direction of the arrow C2 and the outer side rotation drive portion 16e for rotating the R2 installing portion 19 in the direction of the arrow D1 and in the direction of the arrow D2 are arranged. The reagent information stored in the IC tag 27 of the plurality of R3 reagent containers 25 and the reagent information stored in the IC tag 28 of the plurality of R2 reagent containers 26 thus can be reliably read using the inner side antenna section 20 and the outer side antenna section 21.

In the first embodiment, the antenna substrate 20a (21b) is fixed on the surface surrounded by the wall parts 20e (21g) on the side in the direction of the arrow X2 (Y2) of the substrate attachment portion 20b (21c), and the metal plate 22 (23) is attached to the surface on the side in the direction of the arrow X1 (Y1) of the substrate attachment portion 20b (21c), so that the position of the metal plate 22 (23) is fixed with respect to the inner side antenna section 20 (outer side antenna section 21). Therefore, even if the inner side antenna section 20 (outer side antenna section 21) is moved, the relative positional relationship between the metal plate 22 (23) and the inner side antenna section 20 (outer side antenna section 21) does not change and an alignment with respect to each other does not need to be carried out, whereby the reagent information stored in the IC tag 27 of the plurality of R3 reagent containers 25 (reagent information stored in the IC tag 28 of the plurality of R2 reagent containers 26) can be more reliably read using the inner side antenna section 20 (outer side antenna section 21).

In the first embodiment, the metal plate 22 (23) is attached to the substrate attachment portion 20b (21c).
The metal plate 22 (23) thus does not need to be individually arranged for every plurality of R3 reagent containers 25 (plurality of R2 reagent containers 26) to prevent the radio wave emitted from the inner side antenna section 20 (outer side antenna section 21) from reaching the IC tag other than the IC tag to be read, whereby the increase in the number of components can be suppressed. Furthermore, the relative positional relationship between the metal plate 22 (23) and the inner side antenna section 20 (outer side antenna section 21) can be reliably maintained since the metal plate 22 (23) can be attached and fixed to the substrate attachment portion 20b (21c).

In the first embodiment, the metal plate 22 (23) is attached to one side of the substrate attachment portion 20b (21c), and the antenna substrate 20a (21b) is attached to the other side of the substrate attachment portion 20b (21c), so that the metal plate 22 (23) and the antenna substrate 20a (21b) can be suppressed from being proximated to each other unnecessarily (in excess). Therefore, the function of the metal plate 22 (23) can be suppressed from being impaired when the metal plate 22 (23) and the antenna substrate 20a (21b) are unnecessarily brought proximate to each other (in excess).

In the first embodiment, the substrate attachment portion 20b (21c) and the lid member 20c (21d) are both made of resin that can transmit radio waves, and the antenna substrate 20a (21b) is covered by the substrate attachment portion 20b (21c) and the lid member 20c (21d). Therefore, the water droplets from dew condensation can be suppressed from attaching to the antenna substrate 20a (21b) by the substrate attachment portion 20b (21c) and the lid member 20c (21d) covering the antenna substrate 20a (21b) when cooling the reagent with the fan 16f and the peltier element 16g. The short circuit can be suppressed from occurring in the circuit configuring the antenna substrate 20a (21b) due to the water droplets attached to the antenna substrate 20a (21b).

(Second Embodiment)

The second embodiment will be described with reference to FIGS. 23 to 29. In a sample analyzer 301 according to the second embodiment one antenna section 330 is arranged in a reagent installing unit 316 of a measurement mechanism section 302 and a metal plate 331 is attached only on the surface on one side of the antenna section 330.

First, the configuration of a sample analyzer 301 according to the second embodiment of the present invention will be described with reference to FIGS. 23 to 27.

Figure 23:
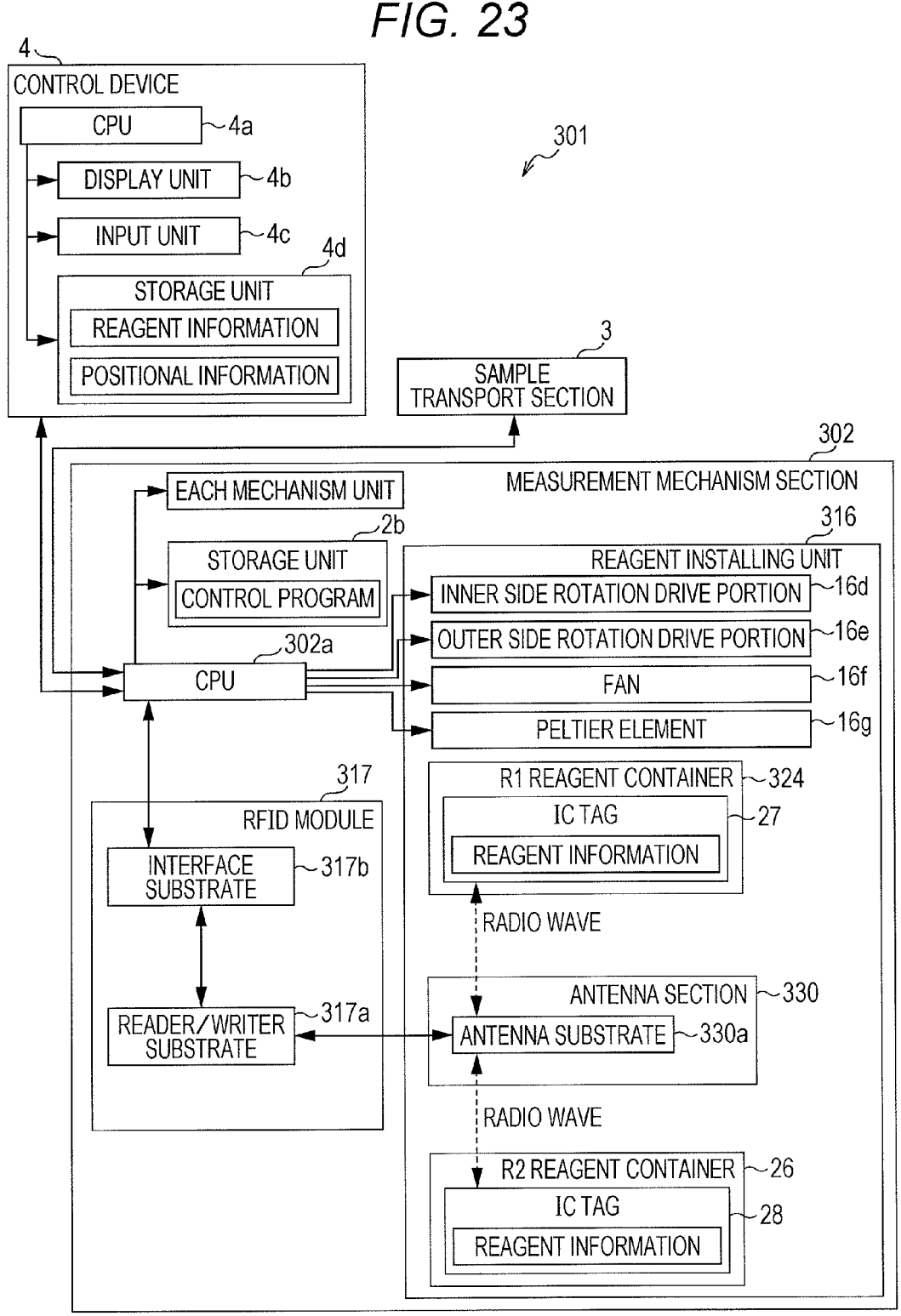
FIG. 23 is a block diagram describing the configuration of the sample analyzer according to a second embodiment of the present invention.
Figure 24:
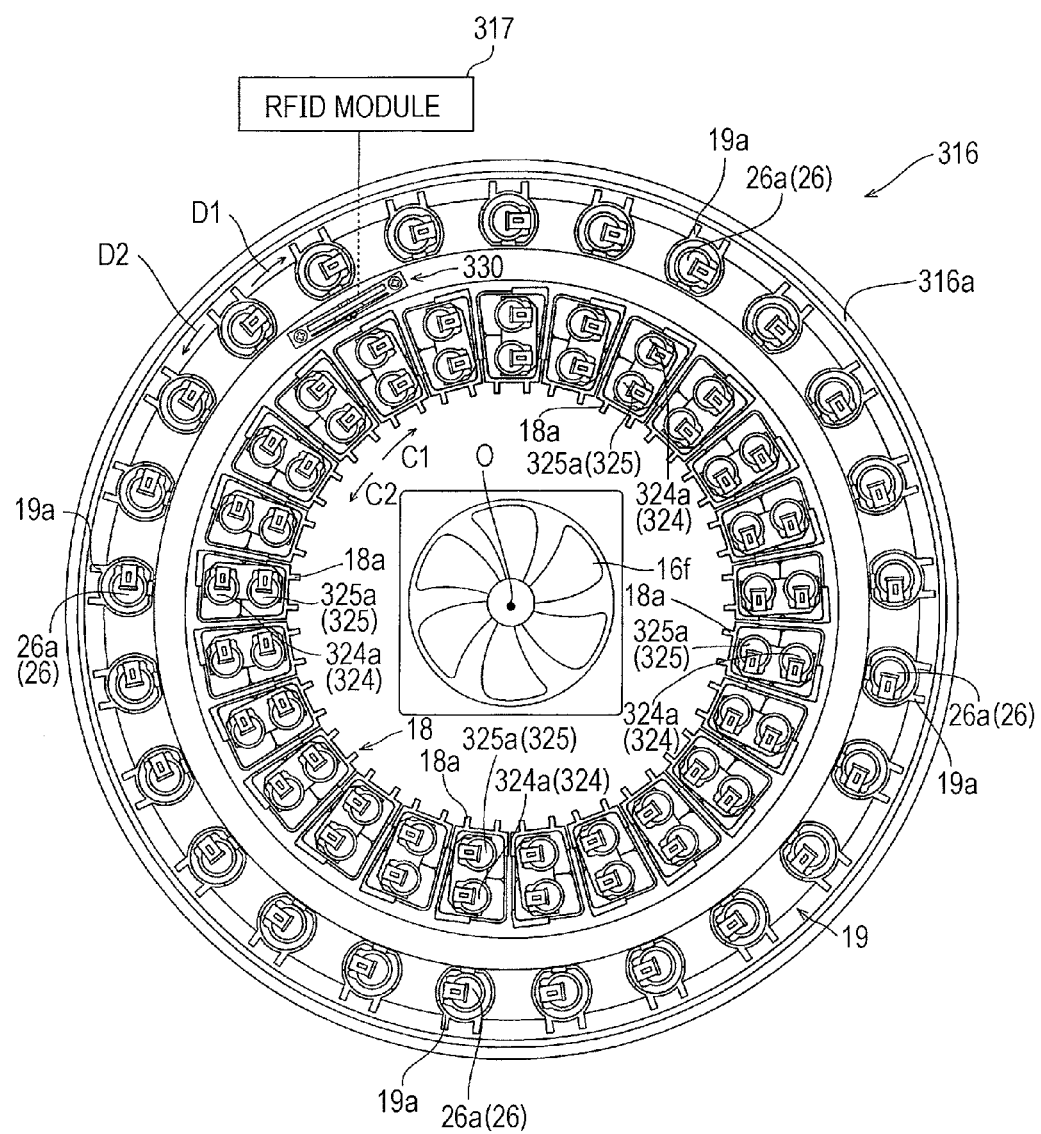
FIG. 24 is a plan view showing an interior of the reagent installing unit of the sample analyzer according to the second embodiment shown in FIG. 23.
Figure 25:
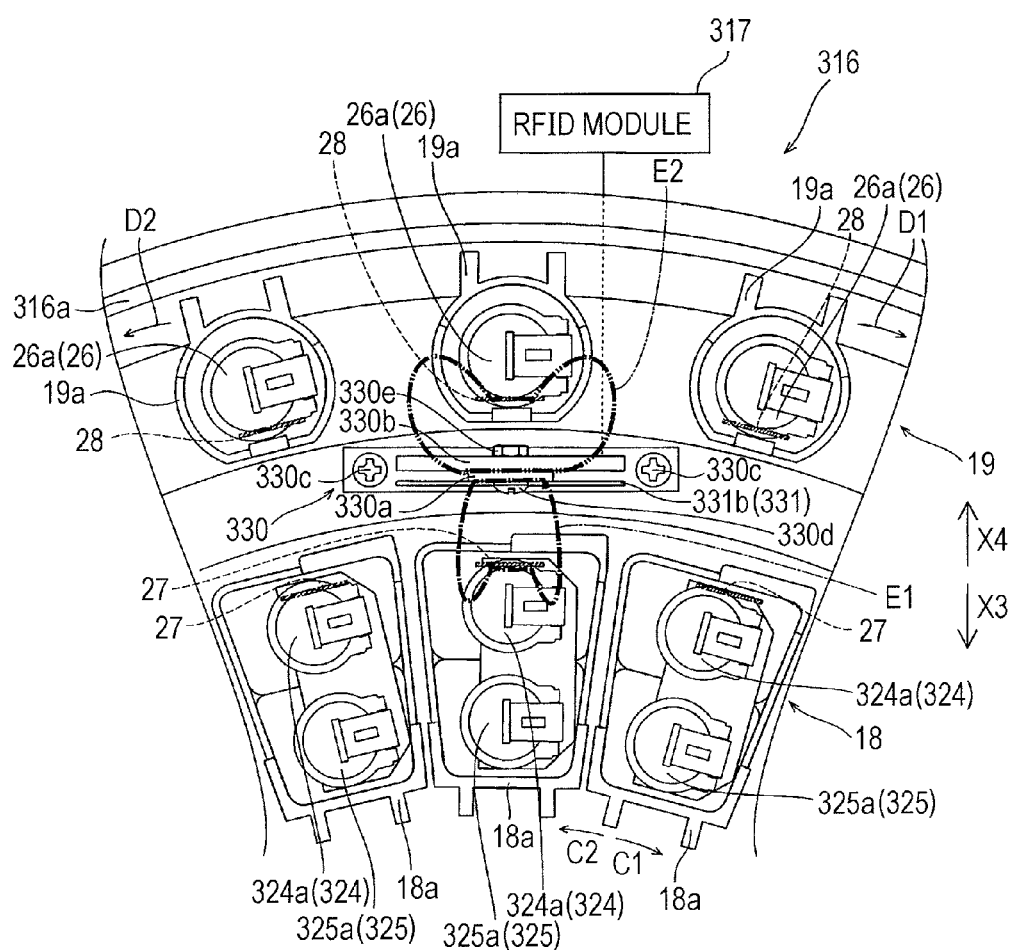
FIG. 25 is an enlarged plan view showing a state of reading the IC tag according to the second embodiment shown in FIG. 23.

As shown in FIG. 23, one antenna section 330 is arranged in the reagent installing unit 316 in the second embodiment. Specifically, as shown in FIG. 24 and FIG. 25, the antenna section 330 is arranged on the outer peripheral side (side opposite to the center O) of the R1/R3 installing portion 18 and on the inner peripheral side of the R2 installing portion 19 inside the housing 316a. In other words, the antenna section 330 is arranged to be sandwiched between the R1/R3 installing portion 18 and the R2 installing portion 19 in plan view. Similar to the first embodiment, the R1/R3 installing portion 18 formed to a substantially circular ring shape is arranged on the inner peripheral side (center O side) of the R2 installing portion 19 formed to a substantially circular ring shape, but a cutout 116a is not formed in the housing 316a as opposed to the first embodiment.

Figure 26:
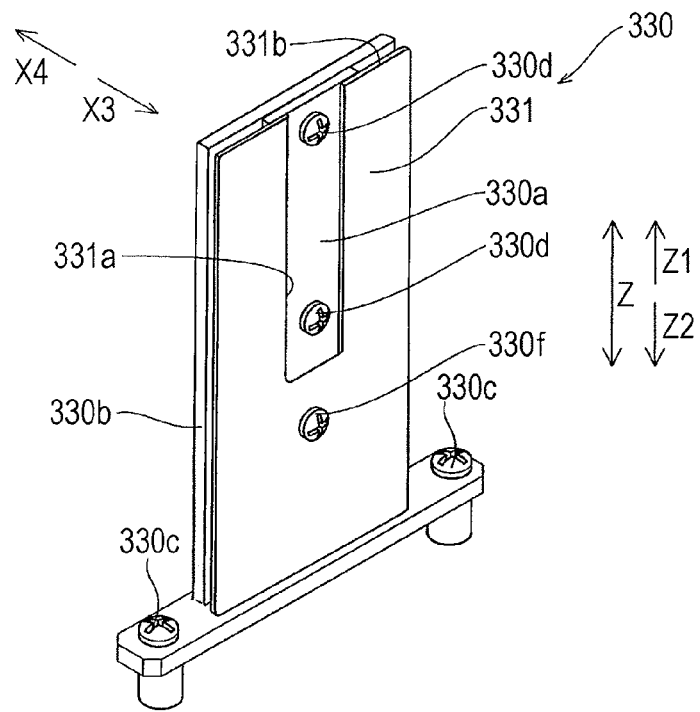
FIG. 26 is a perspective view showing an antenna section of the reagent installing unit according to the second embodiment shown in FIG. 23.
Figure 27:
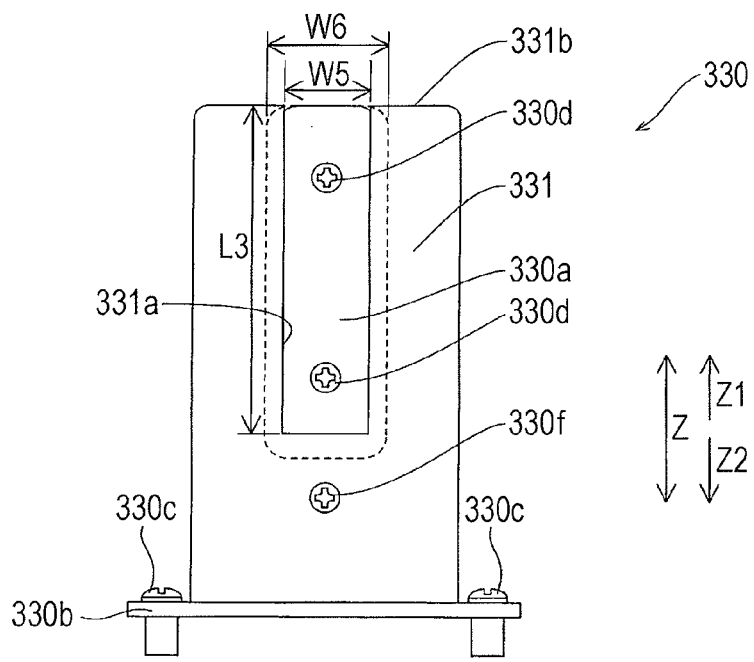
FIG. 27 is a front view showing the antenna section of the reagent installing unit according to the second embodiment shown in FIG. 23.

As shown in FIG. 26 and FIG. 27, the antenna section 330 includes an antenna substrate 330a and a substrate attachment portion 330b for fixing the antenna substrate 330a from the outer side (side in the direction of the arrow X4). The lower part of the substrate attachment portion 330b is fixed to the bottom surface of the housing 316a with a screw 330c.
In other words, the antenna section 330 is fixed to the bottom surface (see FIG. 24) of the housing 316a.

As shown in FIG. 25, the antenna substrate 330a is arranged inside the substrate attachment portion 330b so that the surface on the inner side (side in the direction of the arrow X3) of the antenna substrate 330a faces the R1/R3 installing portion 18, and the surface on the outer side (side in the direction of the arrow X4) of the antenna substrate 330a faces the R2 installing portion 19.

In the second embodiment, the antenna substrate 330a is configured so that the read radio waves and the write radio waves can be emitted from the surface on the side in the direction of the arrow X3 towards the R1/R3 installing portion 18 side (side in the direction of the arrow X3), and so that the read radio waves and the write radio waves can be emitted from the surface on the side in the direction of the arrow X4 towards the R2 installing portion 19 side (side in the direction of the arrow X4). The antenna substrate 330a is configured so that the response radio waves emitted from the IC tags 27 and 28 in response to the read radio waves can be received. The antenna section 330 is thus configured to be able to carry out read and write of the IC tag 27 of the R1 reagent container 324 arranged on the side in the direction of the arrow X3, and to be able to carry out read and write of the IC tag 28 of the R2 reagent container 26 arranged on the side in the direction of the arrow X4. The antenna substrate 330a is connected to a reader/writer substrate 317a of the RFID module 317.

The substrate attachment portion 330b is made of resin that can transmit radio waves. Thus, the read radio waves and the write radio waves emitted from the surface on the side in the direction of the arrow X4 of the antenna substrate 330a towards the R2 installing portion 19 side (side in the direction of the arrow X4), and the response radio waves emitted from the IC tag 28, are transmitted through the substrate attachment portion 330b and reach the R2 installing portion 19 and the antenna substrate 330a. The antenna substrate 330a is fixed to the substrate attachment portion 330b with a screw 330d and a nut 330e.

In the second embodiment, a flat plate-shaped metal plate 331 is attached to the surface on side in the direction of the arrow X3 of the antenna section 330, as shown in FIG. 26. The metal plate 331 is fixed to the substrate attachment portion 330b by a screw 330f and a nut (not shown). The metal plate 331 is made of an aluminum plate material capable of absorbing the radio waves (read radio wave, write radio wave, and response radio wave). As shown in FIG. 27, the metal plate 331 extends in the vertical direction (Z direction) and is formed to a substantially square shape.

The metal plate 331 is formed with a cutout 331a. The cutout 331a is formed by cutting about ⅔ of the entire length in the Z direction of the metal plate 331 from the outer end 331b in the direction of the arrow Z1 of the metal plate 331 to a substantially square shape along the vertical direction (Z direction). The outer end 331b on the side in the direction of the arrow Z1 of the metal plate 331 is thus separated by the cutout 331a. The length L3 in the vertical direction of the cutout 331a is configured to be greater than the width W5 in the horizontal direction of the cutout 331a.

As shown in FIG. 25, the flat plate shaped metal plate 331 is arranged in a region between the antenna section 330 and the R1 reagent container 324 of the R1/R3 installing portion 18 in the second embodiment. The antenna substrate 330a is configured to emit the radio waves towards the R1/R3 installing position 18 side (direction of the arrow X3) through the cutout 331a cut in the vertical direction (Z direction) of the metal plate 331, where the radio waves of the antenna substrate 330a that do not pass the cutout 331a are absorbed by the metal plate 331. Furthermore, the width W5 (see FIG. 27) in the horizontal direction of the cutout 331a is slightly smaller than the width W6 (see FIG. 27) in the horizontal direction of the antenna substrate 330a. The metal plate 331 thus limits the reading range and the writing range on the side in the direction of the arrow X3 by the antenna section 330 (antenna substrate 330a) by limiting the range (range E1 (thick chain dashed line)) in the horizontal direction of the read radio waves and the write radio waves emitted from the antenna substrate 330a towards the side in the direction of the arrow X3.

The metal plate for limiting the reading range and the writing range is not arranged on the side in the direction of the arrow X4 of the antenna section 330. Therefore, the range (range E2 (thick chain double dashed line)) in the horizontal direction of the read radio waves and the write radio waves emitted from the antenna substrate 330a towards the side in the direction of the arrow X4 and the range in the horizontal direction of the response radio wave emitted from the side in the direction of the arrow X4 by the antenna substrate 330a are not limited. As a result, the range E1 (thick chain dashed line) in the horizontal direction of the read radio wave and the write radio wave emitted from the antenna substrate 330a towards the side in the direction of the arrow X3 becomes smaller than the range E2 (thick chain double dashed line) in the horizontal direction of the read radio wave and the write radio wave emitted from the antenna substrate 330a towards the side in the direction of the arrow X4.

As opposed to the first embodiment, in which the IC tag 27 is attached to the R3 reagent container 25, in the second embodiment, the IC tag 27 is attached on the side in the direction of the arrow X4 of the R1 reagent container. The IC tag 27 of the R1 reagent container 324 is attached so as to face the R2 installing portion 19 side (side in the direction of the arrow X4) when the R1 reagent container 324 is arranged in the R1/R3 installing portion 18.

The antenna switching substrate 17c of the first embodiment for switching the antenna section is not necessary in the second embodiment since only one antenna section 330 is arranged. As shown in FIG. 23, the antenna substrate 330a of the antenna section 330 is directly connected to the reader/writer substrate 317a.

Other configurations of the second embodiment are similar to the first embodiment.

In the measurement operation of the sample analyzer 301 according to the second embodiment, the processes other than the reagent information reading process and the reagent aspirating and reagent information writing process are similar to the first embodiment shown in FIG. 20.

Figure 28:
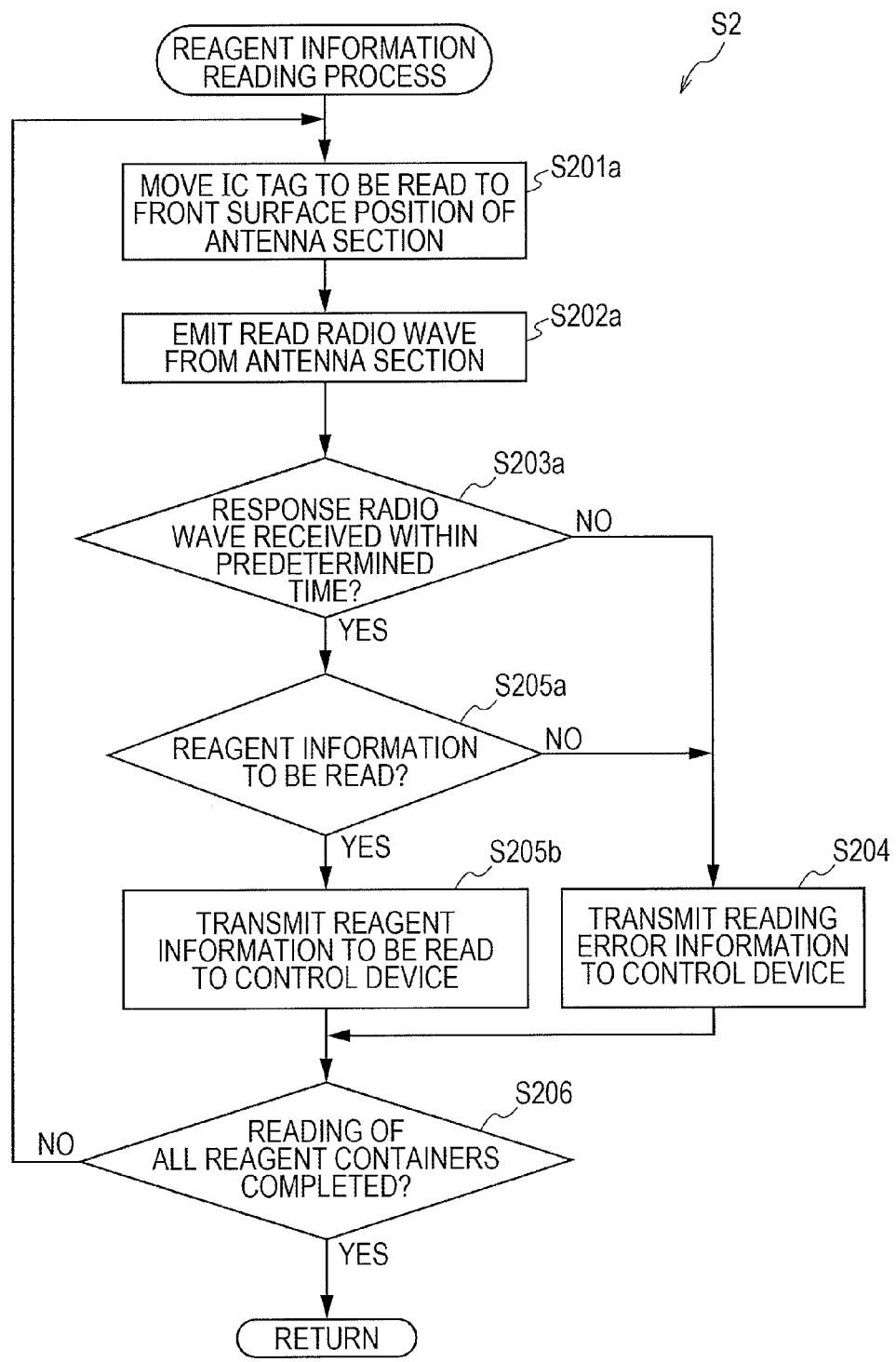
FIG. 28 is a flowchart showing a reagent information reading process of the sample analyzer according to the second embodiment shown in FIG. 23.

With reference to FIG. 25 and FIG. 28, the reagent information reading process of the sample analyzer 301 according to the second embodiment of the present invention will be described in detail.

First, in step S201a, the R1/R3 installing portion 18 (R2 installing portion 19) is rotated in the direction of the arrow C1 (D1) or the direction of the arrow C2 (D2) (see FIG. 25) so that the IC tag 27 (28) to be read is positioned at the position facing the surface on the side in the direction of the arrow X3 (surface on the side in the direction of the arrow X4) of the antenna section 330 by the CPU 302a. In step S202a, the read radio wave is emitted from the antenna section 330 to the IC tag 27 (28) to be read by the CPU 302a.

Thereafter, in step S203a, whether the response radio wave emitted from the IC tag 27 (28) in correspondence with the read radio wave is received within a predetermined time by the antenna section 330 is determined by the CPU 302a. If it is determined that the response radio wave is not received within the predetermined time by the antenna section 330, determination is made that the reading failed, and the reading error information is transmitted to the control device 4 by the CPU 302a in step S204. The process then proceeds to step S206.

If it is determined that the response wave is received within the predetermined time by the antenna section 330, in step S205a, it is determined whether the reagent information contained in the response radio wave received by the antenna section 330 is the reagent information to be read by the CPU 302a. The CPU 302a determines whether the reagent information to be read based on the reagent type contained in the read reagent information. The process proceeds to step S204 if it is determined that the reagent information contained in the response radio wave is not the reagent information to be read. If it is determined that the reagent information contained in the response radio wave is the reagent information to be read, the reagent information to be read contained in the response radio wave is transmitted to the control device 4 in step S205b. The process then proceeds to step S206.

Lastly, in step S206, it is determined by the CPU 302a whether all the reading of 25 IC tags 27 and 25 IC tags 28 is completed. If it is determined that the reading is not yet completed, the process returns to step S201a, and the reading of a new IC tag is carried out. If it is determined that all the reading is carried out, the reagent information reading process is terminated, and the process proceeds to step S3 shown in FIG. 20.

Figure 29:
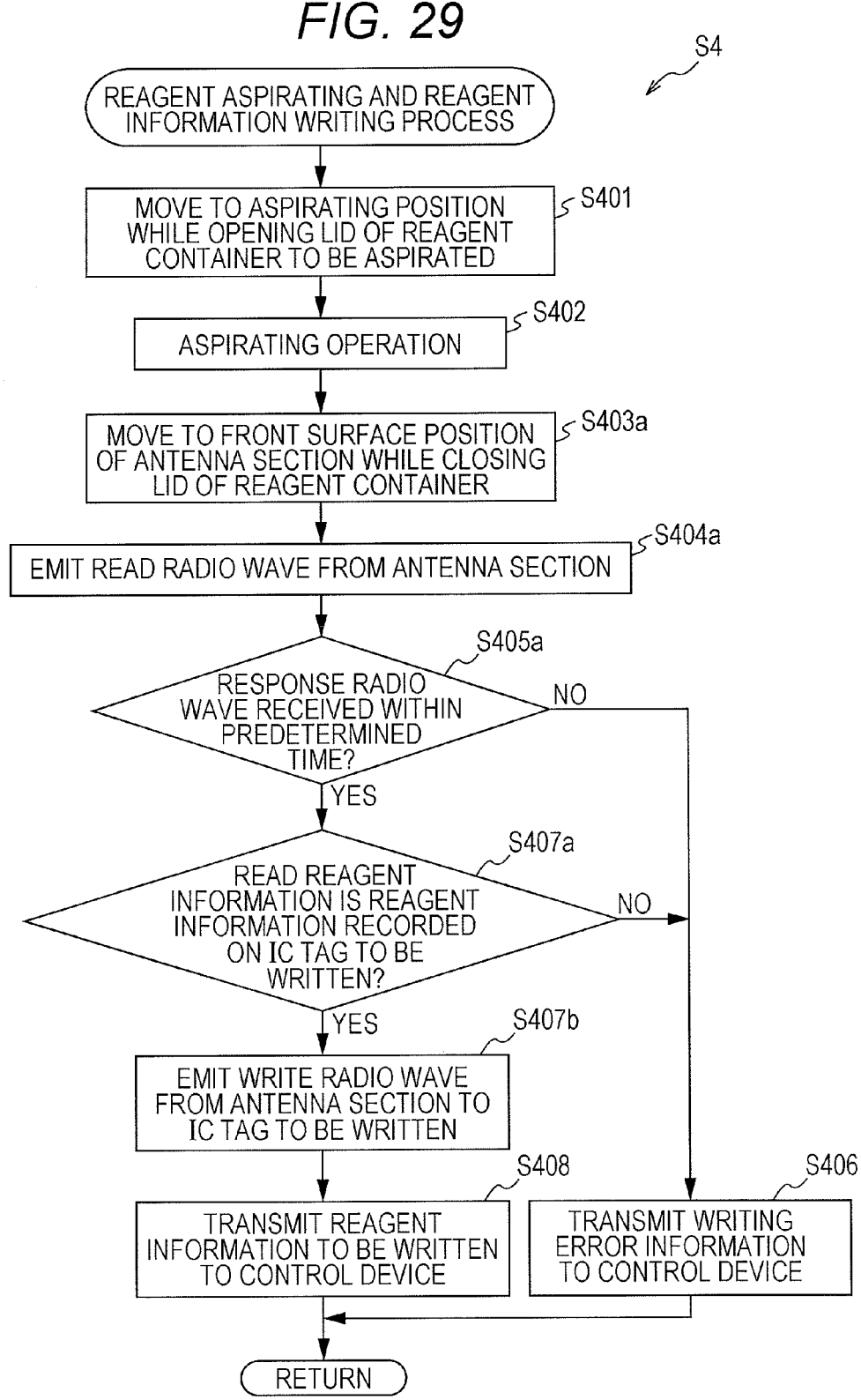
FIG. 29 is a flowchart showing a reagent aspirating and a reagent information writing process of the immune analyzer according to the second embodiment shown in FIG. 23.

With reference to FIG. 25 and FIG. 29, the reagent aspirating and reagent information writing process of the sample analyzer 301 according to the second embodiment of the present invention will be described in detail.

First, in step S401, the R1/R3 installing portion 18 (R2 installing portion 19) is rotated in the direction of the arrow C1 (D1) or the direction of the arrow C2 (D2) (see FIG. 25) so that the R1 reagent container 324 or the R3 reagent container 325 (R2 reagent container 26) to be aspirated is positioned at the aspirating position by the CPU 302a. In this case, the lid 324a of the R1 reagent container 324 or the lid 325a of the R3 reagent container 325 (lid 26a of the R2 reagent container 26) is opened with the rotation of the R1/R3 installing portion 18 (R2 installing portion 19).

In step S402, the R1 reagent or the R3 reagent (R2 reagent) is aspirated. Thereafter, in step S403a, the R1/R3 installing portion 18 (R2 installing portion 19) is rotated in the direction of the arrow C1 (D1) or the direction of the arrow C2 (D2) so that the IC tag 27 (28) to be written by the CPU 302a is positioned at a position facing the surface on the side in the direction of the arrow X3 (surface on the side in the direction of the arrow X4) of the antenna section 330. In this case, the lid 324a of the R1 reagent container 324 or the lid 325a of the R3 reagent container 325 (lid 26a of the R2 reagent container 26) is closed with the rotation of the R1/R3 installing portion 18 (R2 installing portion 19).

In step S404a, the read radio wave is emitted from the antenna section 330 to the IC tag 27 (28) to be written by the CPU 302a. Thereafter, in step S405a, whether the antenna section 330 received the response radio wave within a predetermined time is determined by the CPU 302a. If it is determined that the antenna section 330 did not receive the response radio wave within the predetermined time, the reading error information is transmitted to the control device 4 by the CPU 302a in step S406, and notification that the reagent information cannot be written to the IC tag to be written is displayed on the display unit 4b of the control device 4. The reagent aspirating and reagent information writing process is then terminated, and the process proceeds to step S5 shown in FIG. 20.

If it is determined that the antenna section 330 received the response radio wave within the predetermined time in step S405a, whether the reagent information contained in the response radio wave received by the antenna section 330 is the reagent information recorded on the IC tag to be written by the CPU 302a in step S407a. If it is determined that the reagent information contained in the response radio wave is not the reagent information recorded on the IC tag to be written, the process proceeds to step S406. If it is determined that the reagent information contained in the response radio wave is the reagent information recorded on the IC tag to be written in step S407a, the write radio wave containing the remaining amount information and the like of the reagent is transmitted from the antenna section 330 to the IC tag 27 (28) to be written in step S407b. In step S408, the same information as the reagent information written on the IC tag 27 (28) is transmitted to the control device 4, and then the reagent aspirating and reagent information writing process is terminated, and the process proceeds to step S5 shown in FIG. 20.

In the second embodiment, the antenna section 330 is arranged so as to be sandwiched between the R1/R3 installing portion 18 and the R2 installing portion 19 in plan view, and the flat plate shaped metal plate 331 is arranged between the antenna section 330 and the R1 reagent container 324 of the R1/R3 installing portion 18. The range of the radio wave emitted from the antenna section 330 thus can be limited to the desired range by the metal plate 331, and hence the radio wave emitted from the antenna section 330 can be suppressed from mistakenly reaching the IC tag in which reading of the reagent information does not need to be carried out. Furthermore, since the antenna section 330 for reading the reagent information recorded on the IC tags 27 and 28 can be commonly used, the number of components can be suppressed from increasing by such amount.

In the second embodiment, the R1/R3 installing portion 18 formed to a substantially circular ring shape is arranged on the inner peripheral side of the R2 installing portion 19 formed to a substantially circular ring shape, and the flat plate shaped metal plate 331 is arranged between the antenna section 330 and the R1 reagent container 324 of the R1/R3 installing portion 18, as described above. Thus, when reading the IC tags 27 proximate to each other, the radio wave emitted from the antenna section 330 can be suppressed from mistakenly reaching the IC tag that does not need to be performed with the reading of the reagent information.

Other effects of the second embodiment are similar to the first embodiment.

The embodiments disclosed herein are illustrative and should not be construed as being restrictive in all aspects. The scope of the invention is defined by the scope of the claims rather than by the description of the embodiment, and meaning equivalent to the claims and all modifications within the scope is encompassed herein.

For instance, an example in which the sample analyzer of the present invention is applied to an immune sample analyzer 1 (301) has been shown in the first and second embodiments, but the present invention is not limited thereto. The present invention can be applied as long as it is an apparatus equipped with an antenna section used to read the reagent information of the electronic tag, and may be applied to a blood coagulation analyzer, a urine specimen measurement device, a gene amplifier detection device, and the like other than the immune sample analyzer.

An example in which the metal plates 22 and 23 (331) (limiting member) are made from an aluminum plate material capable of absorbing the radio wave (read radio wave, write radio wave, and response radio wave) is shown in the first and second embodiments, but the present invention is not limited thereto. In the present invention, the limiting member may be configured to be made from a metal member other than aluminum, or may be configured to be made from a metal member and a non-metal member. The limiting member may not include the metal member as long as the radio wave can be limited.

An example in which the cutouts 22a and 23c (331a) (gap) extending to the outer ends 22b and 23d (331b) on the side in the direction of the arrow Z1 are formed in the metal plates 22 and 23 (331) has been shown in the first and second embodiments, but the present invention is not limited thereto. In the present invention, the shape of the cutout of the metal plate is not particularly limited. For instance, the cutout (gap) may be formed to extend to both outer ends in the vertical direction (Z direction). The cutout (gap) may be formed to extend to the outer end in the horizontal direction. The cutout (gap) may also be formed to a curved shape such as to a substantially S shape.

An example in which the cutouts 22a and 23c (331a) (gap) are formed in the metal plates 22 and 23 (331) is shown in the first and second embodiments, but the present invention is not limited thereto. In the present invention, the cutout may not be arranged in the metal plate. For instance, a hole that is not connected with the outer end may be formed in the metal plate as a gap.

An example in which the metal plates 22 and 23 (331) are fixed to the substrate attachment portion 20b of the inner side antenna section 20 and the substrate attachment portion 21c of the outer side antenna section 21 (substrate attachment portion 330b of the antenna section 330) is shown in the first and second embodiments, but the present invention is not limited thereto. In the present invention, the metal plate may not be fixed to the antenna section and may be fixed to one of the housing, the reagent container holder, the reagent container holding member, the reagent container, or the like.

An example in which the width W1 (W5) in the horizontal direction of the cutout 22a (331a) is configured to be slightly smaller than the width W2 (W6) in the horizontal direction of the antenna substrate 20a (330a) is shown in the first and second embodiments, and the width W3 in the horizontal direction of the cutout 23c is configured to be smaller than the width W4 in the horizontal direction of the antenna substrate 21b is shown in the first embodiment, but the present invention is not limited thereto. In the present invention, the width in the horizontal direction of the cutout may be substantially the same as the width in the horizontal direction of the antenna substrate or may be greater than the width in the horizontal direction of the antenna substrate as long as the range of the radio wave emitted from the antenna section can be limited.

An example in which the antenna section 330 is sandwiched between the R1/R3 installing portion 18 and the R2 installing portion 19 in plan view is shown in the second embodiment, but the present invention is not limited thereto. For instance, the antenna section may be arranged on the side opposite to (inner peripheral side) the R2 installing portion of the R1/R3 installing portion, or the antenna section may be arranged on the side opposite to (outer peripheral side) the R1/R3 installing portion of the R2 installing portion.

An example in which the metal plate 331 is arranged in a region between the antenna section 330 and the R1 reagent container 324 of the R1/R3 installing portion 18 is shown in the second embodiment, but the present invention is not limited thereto. In the present invention, the metal plate may be arranged in a region between the antenna section and the R2 reagent container of the R2 installing portion and not in a region between the antenna section and the R1 reagent container of the R1/R3 installing portion. The metal plate may be arranged in both the region between the antenna section and the R1 reagent container of the R1/R3 installing portion and the region between the antenna section and the R2 reagent container of the R2 installing portion.

An example in which the R1/R3 installing portion 18 and the R2 installing portion 19 are arranged in a substantially circular ring shape is shown in the first and second embodiments, but the present invention is not limited thereto. For instance, the R1/R3 installing portion and the R2 installing portion may be arranged to linearly extend in a predetermined direction while being lined side by side.

An example in which 25 R1 reagent containers 24, 25 R3 reagent containers 25, and 25 R2 reagent containers 26 are arranged is shown in the first and second embodiments, but the present invention is not limited thereto. In the present invention, the respective number of the R1 reagent container, the R3 reagent container, and the R2 reagent container may be differed. The number of R1 reagent container (R3 reagent container, R2 reagent container) may be other than 25. For instance, only one of each of the R1 reagent container, the R3 reagent container, and the R2 reagent container may be arranged.

An example in which the R1/R3 installing portion 18 and the R2 installing portion 19 are respectively rotated by the inner side rotation drive portion 16d and the outer side rotation drive portion 16e is shown in the first and second embodiments, but the present invention is not limited thereto. In the present invention, the R1/R3 installing portion and the R2 installing portion may be configured so as to not rotate, and the antenna section may be rotated by arranging a drive portion for rotating the antenna section.

An example in which the metal plate 22 and 23 (metal plate 331) is attached to the inner side antenna section 20 and the outer side antenna section 21 (antenna section 330) is shown in the first and second embodiments, but the present invention is not limited thereto. In the present invention, the antenna section may include the metal plate. In this case, the metal plate (limiting member) may be arranged between the substrate attachment portion and the antenna substrate of the antenna section. For instance, the metal plate (limiting member) may be attached to the surface on the antenna substrate side of the substrate attachment portion. A metal plate (limiting member) may not be provided, and the range of the radio wave emitted from the antenna substrate to the electronic tag may be limited by changing the shape of the antenna substrate.

For instance, the range of the radio wave emitted from the antenna substrate may be limited by forming the antenna substrate to a curved surface.

What is claimed is:

1. A sample analyzer for analyzing a sample using a reagent in a reagent container, comprising:
   a first reagent container holding unit formed to a substantially circular shape in plan view and configured to hold a plurality of first reagent containers arranged in the horizontal direction, each of the first reagent containers includes a first electronic tag having reagent information recorded therein;
   a second reagent container holding unit formed to a substantially circular shape on an inner peripheral side of the first reagent container holding unit in plan view and configured to hold a plurality of second reagent containers arranged in the horizontal direction, each of the second reagent containers includes a second electronic tag having reagent information recorded therein;
   an antenna section configured to transmit a radio wave to an electronic tag of a reagent container held by the first and second reagent container holding unit and receive a radio wave from an electronic tag of a reagent container held by the first and second reagent container holding unit, the antenna section is arranged between the first reagent container holding unit and the second reagent container holding unit;

an RFID module in electrical communication with the antenna and configured to obtain the reagent information recorded on the first electronic tag based on a radio wave received from the first electronic tag via the antenna, and to obtain the reagent information recorded on the second electronic tag based on a radio wave received from the second electronic tag via the antenna; and a first metal plate is arranged in a vertical direction between the antenna section and the first electronic tag of the reagent container held by the first reagent container holding unit, and a second metal plate is arranged between the second electronic tag and the antenna section, the first metal plate is provided with a cutout in the first metal plate for passing the radio wave emitted from the antenna section to the first electronic tag, wherein the cutout is formed to extend in a vertical direction to an end of the first metal plate and the second metal plate is provided with a cutout in the second metal plate for passing the radio wave emitted from the antenna section to the second electronic tag, wherein the metal plate prevents the radio wave emitted by the antenna section from reaching an electronic tag adjacent to the electronic tag which is the target of the reading or writing of the RFID module; and a detector configured to measure a component contained in a measurement sample prepared by the sample and the reagent.

2. The sample analyzer according to claim 1, wherein a width of the cutout is smaller than a width of the antenna section.

3. The sample analyzer according to claim 1, wherein a length of the cutout in a-the vertical direction is greater than a length of the gap in a-the horizontal direction.

4. The sample analyzer according to claim 1, further comprising a drive unit configured to move at least one of the reagent container holding unit and the antenna section.

5. The sample analyzer according to claim 4, wherein a position of the metal plate is fixed with respect to the antenna section.

6. The sample analyzer according to claim 5, wherein the drive unit moves the reagent container holding unit such that an electronic tag which is a target of reading a reagent information is arranged at a position facing the antenna section.

7. The sample analyzer according to claim 5, wherein the antenna section comprises an antenna substrate configured to emit the radio wave, and a substrate attachment portion configured to hold the antenna substrate; and the metal plate is attached to the substrate attachment portion.

8. The sample analyzer according to claim 7, further comprising:

housing configured to accommodate the reagent container holding unit and the antenna section; and a cooling section configured to cool reagents accommodated within the housing, wherein the substrate attachment portion is configured to cover the antenna substrate in a state that the radio wave can be transmitted through the substrate attachment portion.

9. The sample analyzer according to claim 1, wherein the cutout is formed to extend up to one end of the metal plate and not to extend up to other end of the metal member opposite to the one end of the metal plate.

10. The sample analyzer according to claim 1, wherein a width of the cutout is smaller than a width of each reagent container.

11. The sample analyzer according to claim 1, wherein the metal plate is substantially U-shaped.

* * * * *